US008592226B2

(12) United States Patent
Van Duyne et al.

(10) Patent No.: US 8,592,226 B2
(45) Date of Patent: Nov. 26, 2013

(54) SURFACE-ENHANCED RAMAN NANOBIOSENSOR

(75) Inventors: Richard P. Van Duyne, Wilmette, IL (US); Mathew R. Glucksberg, Evanston, IL (US); Karen E. Peltier, Lawrence, KS (US); Christy L. Haynes, Minneapolis, MN (US); Joseph T. Walsh, Evanston, IL (US); Chanda Ranjit Yonzon, Springfield, NJ (US); Nilam C. Shah, Chicago, IL (US); Olga Lyandres, Chicago, IL (US); Douglas A. Stuart, Downer's Grove, IL (US); Jonathan M. Yuen, Chicago, IL (US)

(73) Assignee: Northwestern University, Evanston, IL (US)

( * ) Notice: Subject to any disclaimer, the term of this patent is extended or adjusted under 35 U.S.C. 154(b) by 251 days.

(21) Appl. No.: 12/556,436

(22) Filed: Sep. 9, 2009

(65) Prior Publication Data

US 2010/0087723 A1      Apr. 8, 2010

Related U.S. Application Data

(60) Division of application No. 11/364,978, filed on Mar. 1, 2006, now abandoned, which is a continuation-in-part of application No. 10/652,280, filed on Aug. 29, 2003, now abandoned.

(60) Provisional application No. 60/407,061, filed on Aug. 30, 2002.

(51) Int. Cl.
*G01N 33/553*      (2006.01)

(52) U.S. Cl.
USPC ........... 436/525; 436/518; 436/524; 436/532; 435/14; 435/283.1; 435/287.1

(58) Field of Classification Search
USPC ......... 436/518, 524, 525, 532; 435/14, 283.1, 435/287.1
See application file for complete search history.

(56) References Cited

U.S. PATENT DOCUMENTS

| | | | |
|---|---|---|---|
| 5,830,506 | A | 11/1998 | Taylor |
| 5,846,595 | A | 12/1998 | Sun |
| 5,864,397 | A | 1/1999 | Vo-Dinh |
| 6,011,984 | A | 1/2000 | Van Antwerp |
| 6,025,202 | A | 2/2000 | Natan |
| 6,438,397 | B1 | 8/2002 | Bosquet |
| 6,485,703 | B1 | 11/2002 | Cote |
| 6,544,732 | B1 | 4/2003 | Chee |
| 6,699,724 | B1 | 3/2004 | West |
| 6,764,768 | B2 | 7/2004 | Mrksich |
| 6,849,321 | B2 | 2/2005 | Abbott |
| 6,884,628 | B2 | 4/2005 | Hubbell |

(Continued)

OTHER PUBLICATIONS

Lambert et al., "Measurement of Physiologic Glucose Levels Using Raman Spectroscopy in a Rabbit Aqueous Humor Model," IEEE LEOS Newsletter 12:19 [1998].

(Continued)

*Primary Examiner* — Melanie Y Brown
(74) *Attorney, Agent, or Firm* — Casimir Jones, S.C.

(57) ABSTRACT

The present invention relates to biosensors, in particular to surface-enhanced Raman biosensors for detection of in vivo and ex vivo analytes. In particular, the present invention provides compositions and methods for the in vivo detection of analytes such as glucose.

10 Claims, 29 Drawing Sheets

(56) References Cited

U.S. PATENT DOCUMENTS

| | | | |
|---|---|---|---|
| 6,899,947 B2 | 5/2005 | Wei | |
| 2003/0036199 A1 | 2/2003 | Bamdad | |
| 2003/0219753 A1* | 11/2003 | Quinn et al. | 435/6 |
| 2004/0023293 A1 | 2/2004 | Kreimer | |
| 2005/0227232 A1* | 10/2005 | Babcock | 435/6 |

OTHER PUBLICATIONS

Asher, "UV resonance Raman spectroscopy for analytical, physical, and biophysical chemistry. Part 2," Anal Chem. 65:201A (1993).

Berger et al., "Multicomponent blood analysis by near-infrared Raman spectroscopy," Appl. Opt. 38:2916 (1999).

Mrozek et al., "Detection and identification of aqueous saccharides by using surface-enhanced Raman spectroscopy," Anal. Chem. 74:4069 (2002).

Clarke et al., "Evaluating clinical accuracy of systems for self-monitoring of blood glucose," Diabetes Care 10:622 (1987).

Vanlandingham et al., "Combined Effect of Dorzolamide and Latanoprost on the Rate of Aqueous Humor Flow," Am. J. Opthal. 126:191 (1998).

Baker et al., "Albumin's role in steroid hormone action and the origins of vertebrates: is albumin an essential protein?," FEBS Lett. 439:9 (1998).

Kaufman et al., "A pilot study of the continuous glucose monitoring system: clinical decisions and glycemic control after its use in pediatric type 1 diabetic subjects," Diabetes Care 24:2030 (2001).

Hodneland et al., "Selective immobilization of proteins to self-assembled monolayers presenting active site-directed capture ligands," PNAS 99:5048 (2002).

Haynes et al., "Nanosphere Lithography: A Versatile Nanofabrication Tool for Studies of Size-Dependent Nanoparticle Optics," J. Phys. Chem B 105:5599 (2002).

Malinsky et al., "Chain Length Dependence and Sensing Capabilities of the Localized Surface Plasmon Resonance of Silver Nanoparticles Chemically Modified with Alkanethiol Self-Assembled Monolayers," J. Am. Chem. Soc. 123:1471 (2001).

Lyandres et al., "Real-time glucose sensing by surface-enhanced Raman spectroscopy in bovine plasma facilitated by a mixed decanethiol/mercaptohexanol partition layer," Anal. Chem. 77:6134 (2005).

Sulk et al., "Surface-enhanced Raman Assays (SERA): Measurement of Bilirubin and Salicylate," J. Raman Spec. 30:853 (1999).

Soderholm et al., Raman Spectra of Fructose and Glucose in the Amorphous and Crystalline States, J. Raman Spec. 30:1009 (1999).

Heller et al., "Implanted electrochemical glucose sensors for the management of diabetes," Ann. Rev. Biomed. Eng. 1:153 (1999).

Stuart et al., "Glucose sensing using near-infrared surface-enhanced Raman spectroscopy: gold surfaces, 10-day stability, and improved accuracy," J. Anal. Chem. 77:4013 (2005).

Van Duyne et al., "Atomic Force Microscopy and Surface-Enhanced Raman Spectroscopy," 1993, J. Chem. Phys., vol. 99, Issue 3, pp. 2101-2115.

D'Auria et al., "The Fluorescence Emission of the Apo-glucose Oxidase from *Aspergillus niger* as Probe to Etimate Blucose concentrations," Biochem and Biophys Research Comm. 1999, vol. 263, pp. 550-553.

Graber, et al., "Preparation and Characterization of Au Colloid Monolayers," Anal. Chem., 1995, vol. 67, pp. 735-743.

Russell, et al., A Fluorescence-Based Glucose Biosensor Using Concanavalin A and Dextran Encapsulated in a Poly(ethylene glycol) Hydrogel, Anal. Chem. 1999, vol. 71, pp. 3126-3132.

Malinsky et al., "Chain Length Dependence and Sensing Capabilities of the Localized Surface Plasmon Resonance of Silver Nanoparticles Chemically Modified with Alkanethiol Self-Assembled Monolayers," 2001, J. Am. Chem. Soc. vol. 123, pp. 1471-1482.

Bryant, et al., Surface Raman Scattering of Self-Assembled Monolayers Formed from 1-Alkanethiols at Ag, 1991, J. Am. Chem. Soc. vol. 113, No. 10, pp. 3629-3637.

\* cited by examiner

A  B

SURFACE-ENHANCED RAMAN NANOBIOSENSOR

CROSS-REFERENCE TO RELATED APPLICATIONS

This Application is a divisional application of U.S. patent application Ser. No. 11/364,978, filed Mar. 1, 2006 now abandoned, which in turn is a continuation in part abandoned U.S. patent application Ser. No. 10/652,280, filed Aug. 29, 2003 now abandoned, which in turn claims priority to expired U.S. Provisional Patent Application Ser. No. 60/407,061, filed Aug. 30, 2002, each of which are herein incorporated by reference in their entireties.

STATEMENT REGARDING FEDERALLY SPONSORED RESEARCH OR DEVELOPMENT

This invention was made with government support under National Institute of Health grants EY13002, 13015, and DK066990-01A1, National Science Foundation grants CHE0414554, EEC-0118025 and DMR-0076097, the Air Force Office of Scientific Research MURI program grant F49620-02-1-0381, and the U.S. Army Medical Research and Materiel Command grant W81XWH-04-1-0630. The government has certain rights in the invention.

FIELD OF THE INVENTION

The present invention relates to biosensors, in particular to surface-enhanced Raman biosensors for detection of analytes.

BACKGROUND

In diabetes mellitus, the body either fails to produce or to respond to insulin, which regulates glucose metabolism, resulting in large fluctuations in glucose levels. These fluctuations can cause a range of secondary complications, including kidney disease, heart disease, blindness, nerve damage, and gangrene. Current treatment of diabetes consists of self-regulation of blood glucose levels through frequent monitoring and a combination of diet, medication, and insulin injection, depending on the type of diabetes. Most patients measure their glucose levels by withdrawing small samples of blood using a "finger-stick" apparatus followed by electrochemical detection of an oxidation product of glucose. This type of measurement is both painful and inconvenient. As a result, many patients fail to adequately monitor their glucose levels, risking secondary complications. A faster, easier, and less painful method for frequently measuring glucose levels would be of great individual, clinical, and societal benefit. Continuous monitoring of blood glucose would open the door to feedback control of implanted insulin pumps. In fact, reliable and robust sensor technology is the single stumbling block in an artificial pancreas.

SUMMARY OF THE INVENTION

The present invention relates to biosensors, in particular to surface-enhanced Raman biosensors for detection of analytes.

Accordingly, in some embodiments, the present invention provides a composition comprising a plurality of nanobiosensors, the nanobiosensors configured for surface enhanced Raman spectroscopy detection of an analyte. In some embodiments, the nanobiosensors are coated with a noble metal (e.g., silver, gold, platinum, etc. and combinations thereof). In some embodiments, the nanobiosensors are configured for quantitative detection of the analyte. In some embodiments, the nanobiosensors are configured for use in vivo (e.g., including, but not limited to, implantation of the nanobiosensor under the skin or in the eye). In some embodiments, the nanobiosensors comprise a biocompatible coating. In some embodiments, the nanobiosensors are configured for detection of an analyte in a bodily fluid. In some embodiments, the analyte is glucose. In some embodiments, the analyte is selected from the group consisting of ascorbate, lactic acid, urea, pesticides, chemical warfare agents, pollutants, and explosives, although the systems may be used for the detection of any type of analyte. In some embodiments, the nanobiosensors further comprise a surface bound reversibly-binding analyte receptor, the receptor specific for the analyte of interest. In some embodiments, the analyte is glucose and the reversibly-binding receptor is concanavalin A.

In other embodiments, the nanobiosensors further comprise a self-assembled monolayer formed on the surface of the nanobiosensors. In some embodiments, the self-assembled monolayer is selected from the group consisting of 4-aminothiophenol, L-cystein, 3-mercaptopropionic acid, 11-mercaptoundecanoic acid, 1-hexanethiol, 1-octanethiol, 1-decanethiol (1-DT), 1-hexadecanethiol, mercaptoethanol, poly-DL-lysine, 3-mercapto-1-propanesulfonic acid, benzenethiol, and cyclohexylmercaptan. In other embodiments, the self-assembled monolayer is a combination of two or more components. In some preferred embodiments, the self-assembled monolayer is 1-DT. In other embodiment, the self-assembled monolayer is (1-mercaptoundeca-11-yl)tri (ethylene glycol) $(HS(CH_2)_{11}(OCH_2CH_2)_3OH$. In some embodiments, the nanobiosensors are embedded in nanowells. In some embodiments, the nanowells are fabricated out of silica.

In some embodiments, the nanobiosensors are configured for quantitative detection of glucose or other analytes in a physiological concentration range (e.g., 0-450 mg/dL). In some particularly preferred embodiments, the nanobiosensors are configured for detection of the analyte for at least 3 days. In some embodiments, the nanobiosensors are configured for reversible detection of the analyte. In certain embodiments, the nanobiosensors are configured for detection of the analyte in the presence of interfering molecules, for example, proteins.

The present invention further provides a kit comprising a plurality of nanobiosensors, the nanobiosensors configured for surface-enhanced Raman spectroscopy detection of an analyte.

The present invention also provides a system, comprising a plurality of nanobiosensors, the nanobiosensors configured for surface enhanced Raman spectroscopy detection of an analyte; and a device configured for carrying out the surface-enhanced Raman spectroscopy detection of the analyte. In some embodiments, the device comprises delivery and collection optics, a laser source, a notch filter, and a detector. In some embodiments, the delivery and collection optics and the notch filter are incorporated into a fiber optic probe. In some embodiments, the fiber optic probe is in communication with the laser source and the detector. In some embodiments, the system further comprises a second device configured for the delivery of insulin or other agents to a subject.

The present invention additionally provides a method for detection of an analyte, comprising providing a plurality of nanobiosensors, the nanobiosensors configured for surface-enhanced Raman spectroscopy detection of an analyte; and a device configured for the surface-enhanced Raman spectroscopy detection of the analyte; and contacting the plurality of nanobiosensors with a bodily fluid comprising the analyte; and detecting a surface-enhanced Raman signal from the nanobiosensor using the device. In some embodiments, the level of the surface-enhanced Raman signal is correlated with the concentration of the analyte in the bodily fluid. In some embodiments, the detecting is in vivo. In some embodiments, the nanobiosensors are implanted under the skin. In other embodiments, the nanobiosensors are implanted in an eye.

The present invention further provides a composition comprising a fiber optic tip coated with a plurality of nanobiosensors configured for surface-enhanced Raman spectroscopic detection of glucose. In some embodiments, the nanobiosensors are configured for use in vivo, for example under the skin.

In some embodiments, the present invention provides a composition comprising a biosensor comprising a substrate, and a plurality of nanobiosensors adherent to the substrate, comprising: a plurality of nanospheres; a metal film over nanospheres (MFON); and a self-assembled partition layer formed on the surface of the metal film over nanospheres comprising at least two compounds, wherein the nanobiosensors are configured for the quantitative detection of an analyte such that the spectrum of a surface-enhanced Raman signal detected from the plurality of nanobiosensors in the presence of the analyte is correlated with the concentration of the analyte in a medium. In further embodiments, the substrate is copper or silicon dioxide. In some embodiments, the substrate is configured to provide a plurality of nanowells containing the nanospheres. In other embodiments, the nanospheres comprise polystyrene or silica nanospheres. In further embodiments, the self-assembled partition layer comprises a hydrophilic compound and a hydrophobic compound. In still further embodiments, the hydrophilic compound and the hydrophobic compound comprise modified alkanes. In preferred embodiments, the alkanes comprise a chain length of at least 5 carbon atoms. In particularly preferred embodiments, the hydrophobic compound comprises decanethiol and the hydrophilic compound comprises mercaptohexanol. Other embodiments further comprise a receptor specific for the analyte, wherein the receptor is configured to bind to the analyte reversibly. In a preferred embodiment the analyte is glucose.

In some embodiments, the present invention provides a method for detection of an analyte, comprising providing a biosensor, comprising a substrate, and a plurality of nanobiosensors adherent to the substrate, comprising: a plurality of nanospheres; a metal film over the nanospheres (MFON); and a self-assembled partition layer formed on the surface of the metal film over the nanospheres comprising at least two compounds, wherein the nanobiosensors are configured for the quantitative detection of an analyte such that the spectrum of a surface-enhanced Raman signal obtained from the plurality of the nanobiosensors in the presence of the analyte is correlated with the concentration of the analyte in a medium; and a device configured for the surface-enhanced Raman spectroscopy detection of the analyte; a medium comprising the analyte; and contacting the biosensor with the medium; and detecting a surface-enhanced Raman signal from the biosensor using the device. In some embodiments, the nanospheres comprise polystyrene or silica nanospheres. In other embodiments, the self-assembled partition layer comprises a hydrophilic compound and a hydrophobic compound. In further embodiments, the hydrophilic compound and the hydrophobic compound comprise modified alkanes. In still further embodiments, the alkanes comprise a chain length of at least 5 carbon atoms. In preferred embodiments the hydrophobic compound comprises decanethiol and the hydrophilic compound comprises mercaptohexanol. In another embodiment, the biosensor comprises a receptor specific for the analyte, wherein the receptor is configured to bind to the analyte reversibly. In a preferred embodiment, the analyte is glucose. In a particularly preferred embodiment the detecting is in vivo detecting, and the biosensor is implanted in a subject.

DESCRIPTION OF THE FIGURES

FIG. 2A shows a depiction of a nanosphere monolayer and FIG. 2B shows an atomic force micrograph of the resulting nanoparticle array.

FIG. 6A shows a schematic of nanowell fabrication and FIG. 6B shows an atomic force micrograph of a nanowell structure.

FIG. 12A shows a 1-DT monolayer on AgFON substrate, $\lambda_{ex}$=532 nm, P=1.25 mW, acquisition time (t)=30 seconds. FIG. 12B shows a mixture of 1-DT monolayer and glucose partitioned from a 100 mM solution, $\lambda_{ex}$=532 nm, P=1.25 mW, acquisition time (t)=30 seconds. FIG. 12C shows residual glucose spectrum produced by subtracting FIG. 12A from FIG. 12B. FIG. 12D shows normal Raman spectrum of crystalline glucose for comparison, $\lambda_{ex}$=632.8 nm, P=5 mW, acquisition time (t)=30 seconds.

FIG. 20A shows nanospheres (diameter=390 nm) that have self-assembled to form a hexagonal close packed 2D crystal. Metal (Ag) was then deposited via electron beam deposition. FIG. 20B shows that the FON surface was then incubated in a solution of 1 mM DT in ethanol for 45 minutes and then transferred to 1 mM MH in ethanol for at least 12 hours.

FIG. 21A shows the SERS spectrum of DT/MH-functionalized FON (Day 2). FIG. 21B shows the time-course of intensity of the 1119 cm$^{-1}$ peak. Signal intensities remained stable over a 10 day period with only a 2.08% change in intensity, $\lambda_{ex}$=785 nm, $P_{laser}$=55 mW, acquisition time (t)=2 min.

FIG. 25A SERS spectra of the SAM and glucose at various times. Peaks at 1451 and 1428 cm$^{-1}$ are features of SAM, and 1462 cm$^{-1}$ indicates glucose. Glucose was injected at t=0 sec, and the cell was flushed with bovine plasma at t=225 sec. FIG. 25B shows an expanded scale version of FIG. 25A from 1480 to 1440 cm$^{-1}$. FIG. 25C shows partitioning and departitioning of glucose. $\lambda_{ex}$=785 nm, $P_{laser}$=100 mW, acquisition time (t)=15 sec. The 1/e time constants were calculated to be 28 sec for partitioning, and 25 sec for departitioning.

FIG. 26A shows a rat, with a surgically implanted substrate and optical window integrated into a Raman spectroscopy system consisting of a Ti:Saphire laser ($\lambda_{ex}$=785 nm) band pass filter (BP), steering and collection optics, and a long pass filter (LP) that rejected Raleigh scattered light. FIG. 26B depicts AgFONs used in the in vivo experiments prepared by depositing metal through a mask of self-assembled nanospheres. The resultant structure is shown in the atomic force micrograph in the inset The AgFON was then functionalized by successive emersions in ethanolic solutions of decanethiol and mecaptohexanol. While the present invention is not limited to a particular mechanism of action, and an understanding of the mechanism is not necessary to practice the present invention, it is nonetheless contemplated that glucose is able to partition into and out of the DT/MH layer shown in the left of FIG. 26B.

FIG. 29 depicts the partitioning and departitioning of glucose from the nanobiosensor over time in the presence of varying levels of glucose in the media, with 1/e time constants calculated to be 9 sec for partitioning, and 27 sec for departitioning. ($\lambda_{ex}$=785 nm, P=100 mW, acquisition time (t)=15 s).

GENERAL DESCRIPTION

Figure 1:
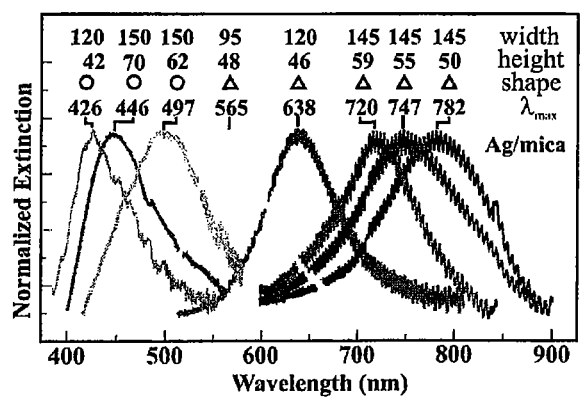
FIG. 1 shows the size and shape of tunable LSPR spectra of Ag nanoparticles fabricated by NSL in some embodiments of the present invention.

The present invention relates to biosensors, in particular to surface-enhanced Raman (SERS) biosensors for detection of in vivo and ex vivo analytes. Because of the clinical importance of the detection of blood glucose, many groups are researching methods for minimally invasive, biologically compatible, quantitative glucose detection (McNichols et al., J. Biomed. Opt. 5:5-16 [2000]; Steffes, Diabetes Tech. Ther. 1:129 [1999]). Mid-infrared absorption, one of the more promising techniques, is sensitive to temperature, pH, and competing absorption by water. Current mid-infrared absorption studies utilize an indwelling probe to minimize complicating factors (Klonoff et al., IEEE LEOS Newsletter 12:13 [1998]). In laser polarimetry, another approach being developed, polarized light is rotated by chiral molecules, such as glucose, while passing through the aqueous humor of the eye. This technique is capable of detecting glucose concentrations as low as 20 mg/dL (~2.0 mM) in vitro, however the optical activity of the other constituents of the aqueous humor, such as ascorbate and albumin, as well as the birefringence of the cornea make this approach extremely difficult (Cameron et al., Diabetes Tech. Ther. 1:125 [1999]). Indirect detection of glucose is also done using fluorescence or other optical techniques (Russell et al., Anal. Chem. 71:3126 [1999]; Jin et al., Anal. Chem. 69:1326 [1997]). These techniques rely on the enzymatic reaction of glucose to produce the detected by-product. Biomolecules similar to the analyte can interfere with this multi-step process, giving false positives.

One technique capable of addressing the major weaknesses of the aforementioned methods (interfering water absorption, overlapping signals from competing analytes, and indirect measurement complications) is by using vibrational Raman spectroscopy. It has been shown that normal Raman spectroscopy (NRS) can readily detect physiological concentrations of glucose in vitro from a simulated aqueous humor solution (Lambert et al., IEEE LEOS Newsletter 12:19 [1998]). Using partial-least squares (PLS), Lambert et al. were able to predict glucose levels ranging from 50 mg/dL (2.8 mM, hypoglycemic) to 1300 mg/dL (72.2 mM, severe diabetic) with a standard error of 24.7 mg/dL (1.5 mM). Berger et al. were able to detect glucose concentrations with an accuracy of 26 mg/dL (1.4 mM) in serum and 79 mg/dL (4.4 mM) in whole blood using PLS (Berger et al., Appl. Opt. 38:2916 [1999]). However, the laser exposure in both experiments is significantly higher than is biologically permissible (American National Standards Institute, Laser institute of America: Orlando, Fla. 1993). The high laser powers and long acquisition times are required due to the inherently small normal Raman scattering cross section of glucose, $5.6 \times 10^{-30}$ cm$^2$ molecule$^{-7}$ sr$^{-1}$ according to McCreery and coworkers (McCreery, R. L. Raman Spectroscopy for Chemical Analysis; John Wiley & Sons, Inc.: New York, 2000; Vol. 157). The reported Raman cross section for glucose is five times smaller than that of benzene and 50 times larger than that of water.

Raman optical activity spectroscopy and Raman difference spectroscopy are both examples of highly sensitive Raman techniques capable of detecting small differences in the Raman cross section. In both of these techniques, however, the resultant difference signals are very small and long data acquisition times are required (Bell et al., Carbohydr. Res. 257:11 [1994]; Chaiken et al., Proc. SPIE 4254:216 [2001]). Such an approach is not desirable in a rapid, robust, clinical analysis method. One way to increase the Raman cross section is to exploit resonance Raman spectroscopy (Asher, Anal chem. 65:201 A [1993]). In the case of glucose, this would require excitation in the deep ultraviolet region ($\lambda$~200 nm) of the spectrum. However, ultraviolet excitation is unlikely to be appropriate for in vivo sensing due to photodamage of DNA.

The compositions and methods of the present invention overcome these limitations by employing surface enhanced Raman spectroscopy (SERS). SERS retains all of the advantages of normal Raman spectroscopy while achieving significantly stronger signal intensity. SERS is a process whereby the Raman scattering signal is increased when a Raman-active molecule is spatially confined within range of the electromagnetic fields generated upon excitation of the localized surface plasmon resonance of nanostructured noble metal surfaces. The ensemble averaged Raman signal increases by up to eight orders of magnitude while the non-ensemble-averaged Raman signal can increase by 14 or 15 orders of magnitude in special cases (Emory and Nie, Science 275: 1102 [1997]; Kneipp et al., Phys. Rev. Lett. 78:1667 [1997]). Both chemical and conformational information can be elucidated from SERS. Theoretical analysis suggests that molecules confined within the decay length of the electromagnetic fields, viz. 0-4 nm, will exhibit SER spectra even if they are not chemisorbed (Schatz et al., In Handbook of Vibrational Spectroscopy; Chalmers, J. M., Griffiths, P. R. Eds.; John Wiley & Sons: Chichester, UK, 2002; Vol. 1 pp 759-774). SERS possesses many desirable characteristics as a tool for the chemical analysis of in vivo molecular species including high specificity, attomole to high zeptomole mass sensitivity, micromolar to picomolar concentration sensitivity, and interfacial generality (Smith and Rodger, In Handbook of Vibrational Spectroscopy; Chalmers, J. M., Griffiths, P. R. Eds.; John Wiley & Sons: Chichester, UK, 2002; Vol. 1 pp 775-784).

Experiments conducted during the course of development of the present invention that sought to observe glucose on silver film over nanosphere (AgFON) surfaces using SERS without a partition layer were unsuccessful. This result is in agreement with all previous attempts to measure glucose using SERS that are known. Published SERS spectra of glucose use a multi-step surface preparation technique that is likely to be rather unwieldy for field or clinical applications (Mrozek et al., Anal. Chem. 74:4069 [2002]). The present invention is not limited to a particular mechanism of action. Indeed, an understanding of the mechanism is not necessary to practice the present invention. Nonetheless, it is contemplated that, based on the described substrate preparation and the resultant SER spectra in Mozek et al., it is possible that recrystallized rather than adsorbed glucose was observed. Historic difficulty of SERS detection of glucose is likely to be attributable to its weak or non-existent binding to bare silver surfaces since its normal Raman cross section should provide sufficient signal.

Figure 11:
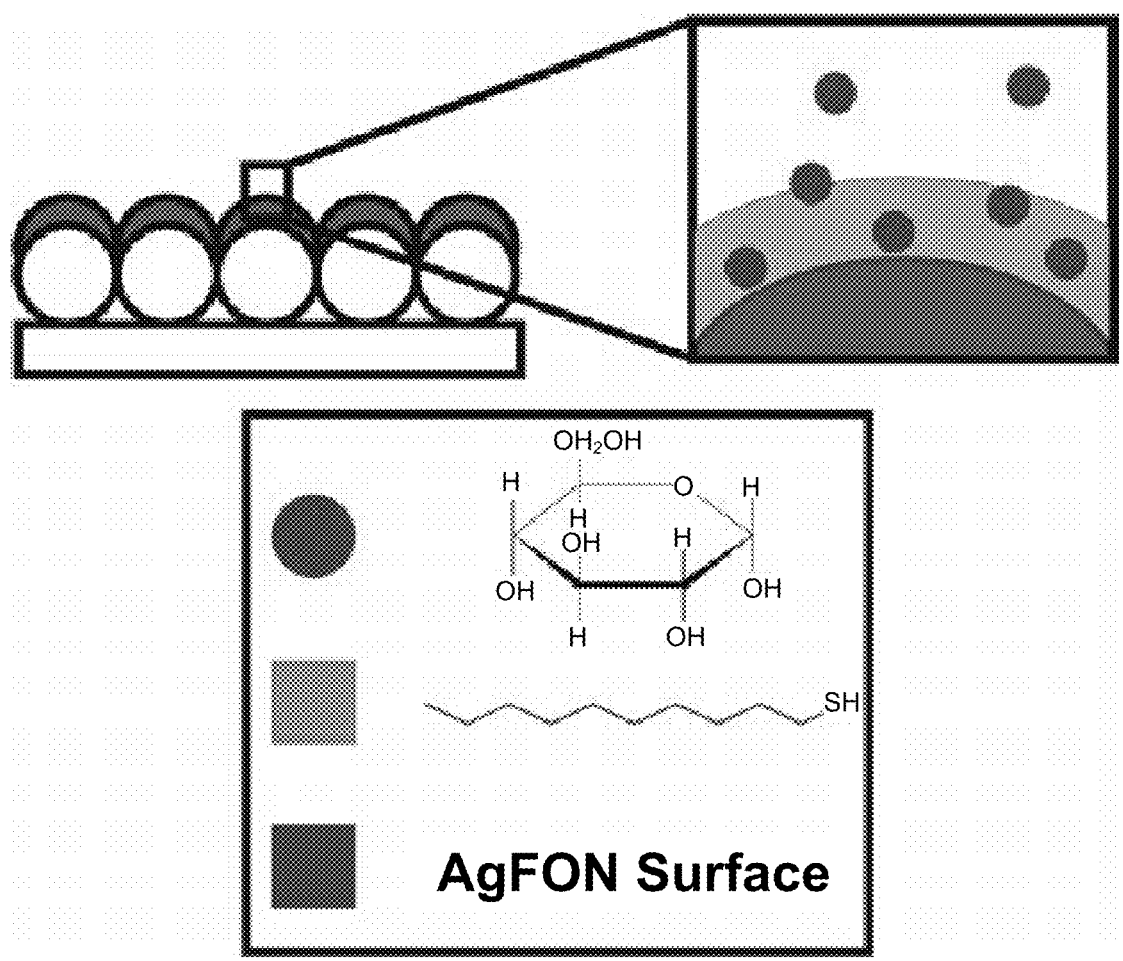
FIG. 11 shows hypothetical glucose concentration gradient created by 1-DT capture layer.

The present invention provides novel methods for increasing glucose interaction with the AgFON surface, such as the formation of a self-assembled monolayer (SAM) on the surface of biosensors to pre-concentrate the analyte of interest (See e.g., FIG. 11), in a manner analogous to that used to create the stationary phase in high performance liquid chromatography (HPLC) (Freunshct et al. Chem. Phys. Lett. 281: 372 [1997]; Blanco et al., J. Anal. Chim. Acta 436:173 [2001]; Yang et al., Anal. Chem. 34:1326 [1995]; Carron et al., J. Anal. Chem. 67:3353 [1995]; Deschaines et al., Appl. Spectrosc. 51:1355 [1997]). Experiments conducted during the course of development of the present invention demonstrated that SERS can be utilized for the detection of analytes such as glucose. The present invention thus provides improved methods of detecting physiologically relevant analytes.

Further experiments conducted during the course of development of the present invention (See Example 2) demonstrated quantitative detection of glucose in the physiological range (0-450 mg/dL, 0-25 mM) under physiological conditions, three-day sensor stability, partition/departition efficacy of the sensor, and glucose detection in the presence of an interfering protein.

The accuracy of the SERS glucose sensor was evaluated using the Clarke error grid, the accepted metric for judging the prediction capability of glucose sensors in the clinical concentration range (Clarke et al., Diabetes Care 10:622 [1987]). 94% of the predictions fell in zones A and B, signifying that correct treatment choices can be made using this sensor. Additionally, the EG3-modified AgFON sensor quantitatively detects glucose in the physiological range with a corresponding prediction error of 82 mg/dL (4.5 mM). The stability of the EG3-modified AgFON SERS substrate is evident as the SERS bands and intensities do not change significantly during a three-day period in saline with pH=7.4 at room temperature. The molecular order of the EG3 SAM increases with incubation time (Biebuyck et al., Langmuir 10:1825 [1994]), and this rearrangement gives rise to slightly larger SERS intensities. The glucose partition/departition capability of the EG3-modified AgFON sensor was demonstrated by exposing the sensor to cycles of 250 mM and 0 mM glucose solutions. The relatively high glucose concentration used in this experiment caused incomplete departitioning after each cycle, and accordingly, the glucose accumulated in each step. The present invention is not limited to a particular mechanism. Indeed, an understanding of the mechanism is not necessary to practice the present invention. Nonetheless, it is contemplated that physiological concentrations of glucose will not likely cause such accumulation in the partition layer, and the natural flow of aqueous humor (Vanlandingham et al., Am. J. Opthal. 126:191 [1998]) or interstitial fluid will assist glucose departitioning. This work further demonstrates that an EG3 partition layer can capture glucose near the surface, while showing resistance to serum albumin, the most abundant protein in plasma (Baker et al., FEBS Lett. 439:9 [1998]).

The present invention further provides methods for the simultaneous detection of multiple (e.g., two or more) analytes. In some embodiments, the nanobiosensors contain arrays of regions, where each region is specific for the detection of a different analyte. The nanobiosensors can then be scanned with a detection device to obtain information about the concentration of multiple analytes.

DEFINITIONS

As used herein, the term "nanobiosensors," as in "nanobiosensors configured for surface enhanced Raman spectroscopy detection of an analyte" refers to any sensor that is small enough to be implanted internally (e.g., under the skin or in the eye), is specific for detection of one or more analytes, and is capable of having an altered surface enhanced Raman signal in the presence of the specific analyte(s). In preferred embodiments, the nanobiosensors comprise components for specifically, but reversibly, interacting with the specific analyte.

As used herein, the term "surface bound reversibly-binding receptor" refers to a receptor bound to the surface of a nanobiosensor of the present invention that binds reversibly to a specific analyte. In preferred embodiments, the interaction of the receptor and the analyte lasts long enough for detection of the analyte by the sensor.

As used herein, the term "self-assembled monolayer" refers to a material that forms single layer or multilayers of molecules on the surface of a nanobiosensor. As used herein, the term "self-assembled partition layer" refers to material that forms a layer or multilayers on the surface of a nanobiosensor.

As used herein, the term "nanowell" refers to a solid surface comprising wells for immobilizing the nanobiosensors of the present invention. In preferred embodiments, the nanowells are made of an inert material and are large enough to hold a plurality of nanobiosensors.

As used herein, the term "bodily fluid" refers to any fluid normally found in the body of a mammal (e.g., a human). Exemplary bodily fluids include, but are not limited to, blood, serum, lymph, aqueous humor, interstitial fluid, and urine. The term "bodily fluid" encompasses both bodily fluid found in its natural state (e.g., in the body) and bodily fluid removed from the body.

As used herein, the term "analyte" refers to any molecule or atom or molecular complex suitable for detection by the nanobiosensors of the present invention. Exemplary analytes include, but are not limited to, various biomolecules (e.g., proteins, nucleic acids, lipids, etc.), glucose, ascorbate, lactic acid, urea, pesticides, chemical warfare agents, pollutants, and explosives.

As used herein, the term "a device configured for the detection of surface enhanced Raman scattering signal from said nanobisoensors" refers to any device suitable for detection of a signal from the nanobiosensors of the present invention. In some embodiments, the device includes delivery and collection optics, a laser source, a notch filter, and detector.

As used herein, the term "instructions for using said kit for detection of said analyte" includes instructions for using the nanobiosensors and devices of present invention for the detection of any suitable "analyte." In preferred embodiments, the instructions include instructions for the quantitative detection of the analyte. In some embodiments, the instructions further comprise the statement of intended use required by the U.S. Food and Drug Administration (FDA) in labeling medical devices. The FDA requires that medical devices be approved through the 510(k) procedure. Information required in an application under 510(k) includes: 1) The product name, including the trade or proprietary name, the common or usual name, and the classification name of the device; 2) The intended use of the product; 3) The establishment registration number, if applicable, of the owner or operator submitting the 510(k) submission; the class in which the product was placed under section 513 of the FD&C Act, if known, its appropriate panel, or, if the owner or operator determines that the device has not been classified under such section, a statement of that determination and the basis for the determination that the product is not so classified; 4) Proposed labels, labeling and advertisements sufficient to describe the diagnostic product, its intended use, and directions for use, including photographs or engineering drawings, where applicable; 5) A statement indicating that the device is similar to and/or different from other products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

As used herein, the term "physiological concentration range" refers to the concentration range of an analyte that is typically found in an animal (e.g., a human). The physiological concentration range covers both the physiological concentration in a healthy animal and in an animal with a disease (e.g., diabetes).

As used herein, the term "detection of said analyte for at least 3 days" refers to nanobiosensors of the present invention that are capable of detecting an analyte for at least 3 days in vitro or in vivo. Detection of said analyte for at least 3 days does not require that the nanobiosensor take continuous measurements for 3 days, but that the sensor functions (e.g., by taking periodic measurements) for at least 3 days. In preferred embodiments, the measurements are quantitative and maintain precision and accuracy for at least 3 days.

As used herein, the term "reversible detection of said analyte" refers to nanobiosensors of the present invention that are capable of repeated detection of an analyte. For example, in some embodiments, nanobiosensors measure the concentration of glucose in a biological fluid multiple times (e.g., from one time per second to one time per hour) over the course of the usable life span of the sensor (e.g., at least 3 days).

As used herein, the term "detection of said analyte in the presence of interfering proteins" refers to nanobiosensors of the present invention that are able to function in the presence of proteins other than the analyte (e.g., biological proteins).

As used herein, the term "biological macromolecule" refers to large molecules (e.g., polymers) typically found in living organisms. Examples include, but are not limited to, proteins, nucleic acids, lipids, and carbohydrates.

A "solvent" is a liquid substance capable of dissolving or dispersing one or more other substances. It is not intended that the present invention be limited by the nature of the solvent used.

As used herein, the term "polymer" refers to material comprised of repeating subunits. Examples of polymers include, but are not limited to polyacrylamide and poly(vinyl chloride), poly(vinyl chloride) carboxylated, and poly(vinyl chloride-co-vinyl acetate co-vinyl) alcohols.

As used herein, the term "polymerization" encompasses any process that results in the conversion of small molecular monomers into larger molecules consisting of repeated units. Typically, polymerization involves chemical crosslinking of monomers to one another. As used herein, the term "spectrum" refers to the distribution of electromagnetic energies arranged in order of wavelength.

As used the term "visible spectrum" refers to light radiation that contains wavelengths from approximately 360 nm to approximately 800 nm.

As used herein, the term "ultraviolet spectrum" refers to radiation with wavelengths less than that of visible light (i.e., less than approximately 360 nm) but greater than that of X-rays (i.e., greater than approximately 0.1 nm).

As used herein, the term "infrared spectrum" refers to radiation with wavelengths of greater than 800 nm.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "medium" refers to the fluid environment of an analyte of interest. In some embodiments, the medium refers to a bodily fluid. The bodily fluid may be, for example, blood, plasma, serum, cerebrospinal fluid, vitreous or aqueous humor, urine, extracellular fluid, or interstitial fluid. In some embodiments, the medium is an in vivo medium. In other embodiments, the medium is an ex vivo or in vitro medium, for example, a fluid sample taken from a subject.

DETAILED DESCRIPTION OF THE INVENTION

The present invention relates to biosensors, in particular to surface-enhanced Raman scattering (SERS) biosensors for detection of intracellular analytes. The compositions and methods of the present invention provide sensitive, real time measurement of physiologically relevant analytes such as glucose.

I. Surface-Enhanced Raman Spectroscopy

In some embodiments, the present invention provides nanobiosensors that utilize surface-enhanced Raman spectroscopy to detect intracellular analytes.

A. Localized Surface Plasmon Resonance

The signature optical property of a noble metal nanoparticle is the localized surface plasmon resonance (LSPR). This resonance occurs when the correct wavelength of light strikes a noble metal nanoparticle, causing the plasma of conduction electrons to oscillate collectively. The term LSPR is used to emphasize that this collective oscillation is localized within the near surface region of the nanoparticle and to differentiate it from propagating surface plasmons which are often referred to simply as surface plasmons. The two consequences of LSPR excitation are: 1) selective photon absorption and 2) generation of locally enhanced or amplified electromagnetic fields at the nanoparticle surface. The LSPR for noble metal nanoparticles in the 20-few hundred nanometer size regime occurs in the visible and IR regions of the spectrum and can be measured by UV-visible-IR extinction spectroscopy (FIG. 1) (Haynes et al., J. Phys. Chem. B105:5599 [2001]). The spectral location of the LSPR is intricately related to the resulting SERS spectrum.

B. Nanosphere Lithography

Figure 2:
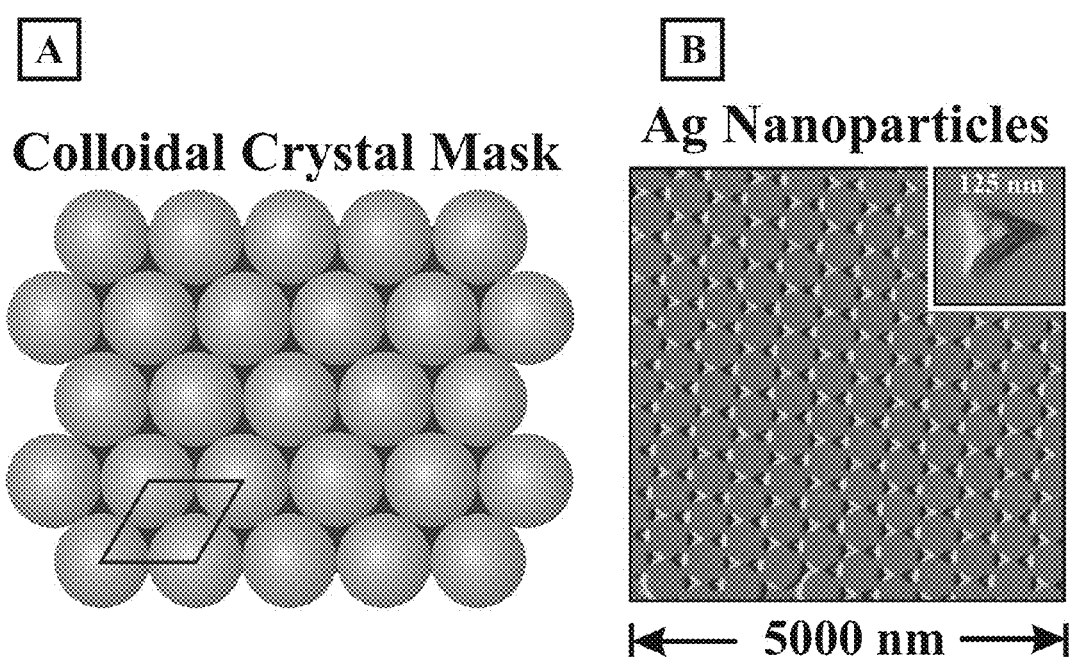
FIG. 2 depicts exemplary steps in nanosphere lithography.

Nanosphere lithography (NSL) is a fabrication technique to inexpensively produce nanoparticle arrays with precisely controlled shape, size, and interparticle spacing, and accordingly precisely controlled LSPRs (Hulteen et al., J. Vac. Sci. Technol. A 13:1553 [1995]). The need for monodisperse, reproducible, and materials general nanoparticles has driven the development and refinement of the most basic NSL architecture as well as many new nanostructure derivatives. Every NSL structure begins with the self-assembly of size-monodispersed nanospheres to form a two-dimensional colloidal crystal deposition mask (FIG. 2A). As in all naturally occurring crystals, nanosphere masks include a variety of defects that arise as a result of nanosphere polydispersity, site randomness, point (vacancy) defects, line defects (slip dislocations) and polycrystalline domains. Typical defect-free domain sizes are in the 10-100 micron range. Following self-assembly of the nanosphere mask, a noble metal or other material is then deposited by thermal evaporation, electron beam deposition, or pulsed laser deposition from a source normal to the substrate through the nanosphere mask to a controlled mass thickness, $d_m$. After noble metal deposition, the nanosphere mask is removed by sonicating the entire sample in a solvent, leaving behind the material deposited through the nanosphere mask to the substrate (FIG. 2B). The LSPR of NSL-derived nanoparticles depends on nanoparticle material, size, shape, interparticle spacing, substrate, solvent, dielectric thin film overlayers, and molecular adsorbates (Haynes et al., supra).

C. Surface-Enhanced Raman Scattering

Figure 3:
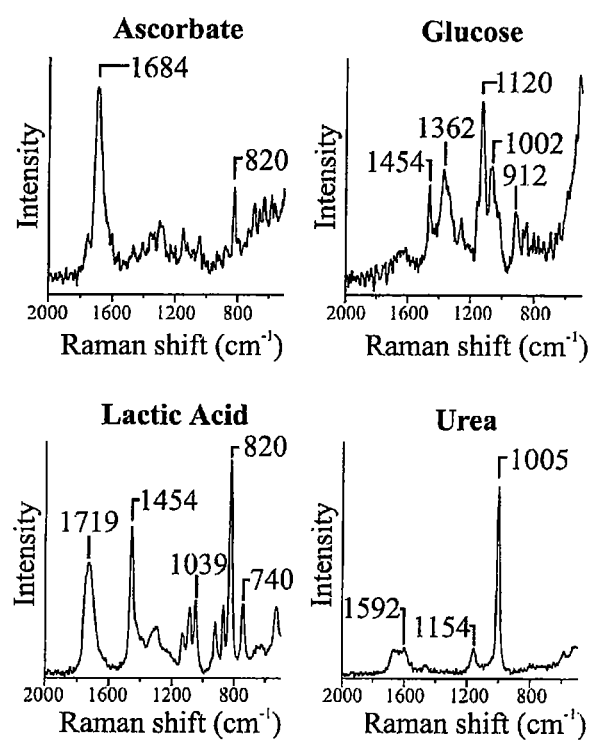
FIG. 3 shows FT-Raman spectra of the major components of the aqueous humor.

Normal Raman scattering is an inelastic scattering process in which photons incident on a sample transfer energy to or from the sample's vibrational or rotational modes. Individual bands in a Raman spectrum are characteristic of specific molecular motions. As a result, each chemical analyte has its own unique Raman signature. For example, the four biochemicals commonly found in aqueous humor each have very different Raman spectra (FIG. 3). When a Raman-active molecule is positioned within the electromagnetic fields generated upon excitation of the LSPR of NSL-derived nanoparticles, the Raman signal increases by up to eight orders of magnitude. Both chemical and conformational information can be elucidated from SERS data. Current estimates suggest that the electromagnetic fields reach further than 65 nanometers from the noble metal surface, allowing one to probe molecular species using the surface of embedded nanoparticles (Malinsky et al., J. Am. Chem. Soc. 123:1471 [2001]). SERS possesses many desirable characteristics as a tool for the chemical analysis of in vivo molecular species including high specificity, attomole to high zeptomole mass sensitivity, micromolar to picomolar concentration sensitivity, and interfacial generality (Handbook of Vibrational Spectroscopy; Chalmers, J. M., Griffiths, P. R. Eds.; John Wiley & Sons: Chichester, UK, 2002; Vol. 1 pp 392).

In order to evaluate the potential of embedded nanoparticle multianalyte SERS sensors, it is preferred to consider the theoretical SERS signal from physiologically relevant analyte concentrations. The ocular in vivo concentrations of glucose, lactate, urea, ascorbate, and protein have not been evaluated in humans. The sensing mechanism of the present invention allows determination of these concentrations. In some embodiments, the intensity of the SERS signal is calculated using the following equation (Van Duyne, R. P. In Chemical and Biochemical Applications of Lasers; Moore, C. B. Ed.; Academic Press: New York, 1979; Vol. 4, pp 101-184).

$$I_{if}(\omega_s) = \Omega \frac{d\sigma(\omega_s)}{d\Omega} N_{surf} P_L(\omega_L) \varepsilon(\omega_L)^{-1} QT_m T_o EF$$

In this equation, $I_{if}(\omega_s)$ is the intensity of the SERS peak in photoelectron counts per second, $N_{surf}$ is the number of molecules in the probed area of the surface, $\Omega(d\sigma(\omega_s)/d\Omega)$ is the scattering cross-section in molecules$^{-1}$ (accounting for the solid collection angle in steradians and illumination area in cm$^2$), $P_L(\omega_L) \in (\omega_L)^{-1}$ describes the photon flux in photons per second, $QT_m T_o$ describes the efficiency of the detection system (unitless), and EF is the enhancement factor (unitless). Using a Raman cross-section of $10^{-30}$ cm$^2$sr$^{-1}$ molecule$^{-1}$, an enhancement factor of $10^8$, and the expected collection parameters, a conservative estimate of the glucose detection limit is $1.51 \times 10^{-2}$ mg/dL. This value is almost three orders of magnitude lower than the expected physiological concentration of 97 mg/dL (in rabbits) (Lambert et al., IEEE LEOS Newsletter 12:19 [1998]). It is contemplated that lactate, urea, and ascorbate have similar detection limits. The present invention thus provides methods for simultaneously detecting and quantitating a variety of analytes for both fundamental and applied circumstances.

D. Optimum Parameters for Biocompatible SERS Nanosensors

Figure 4:
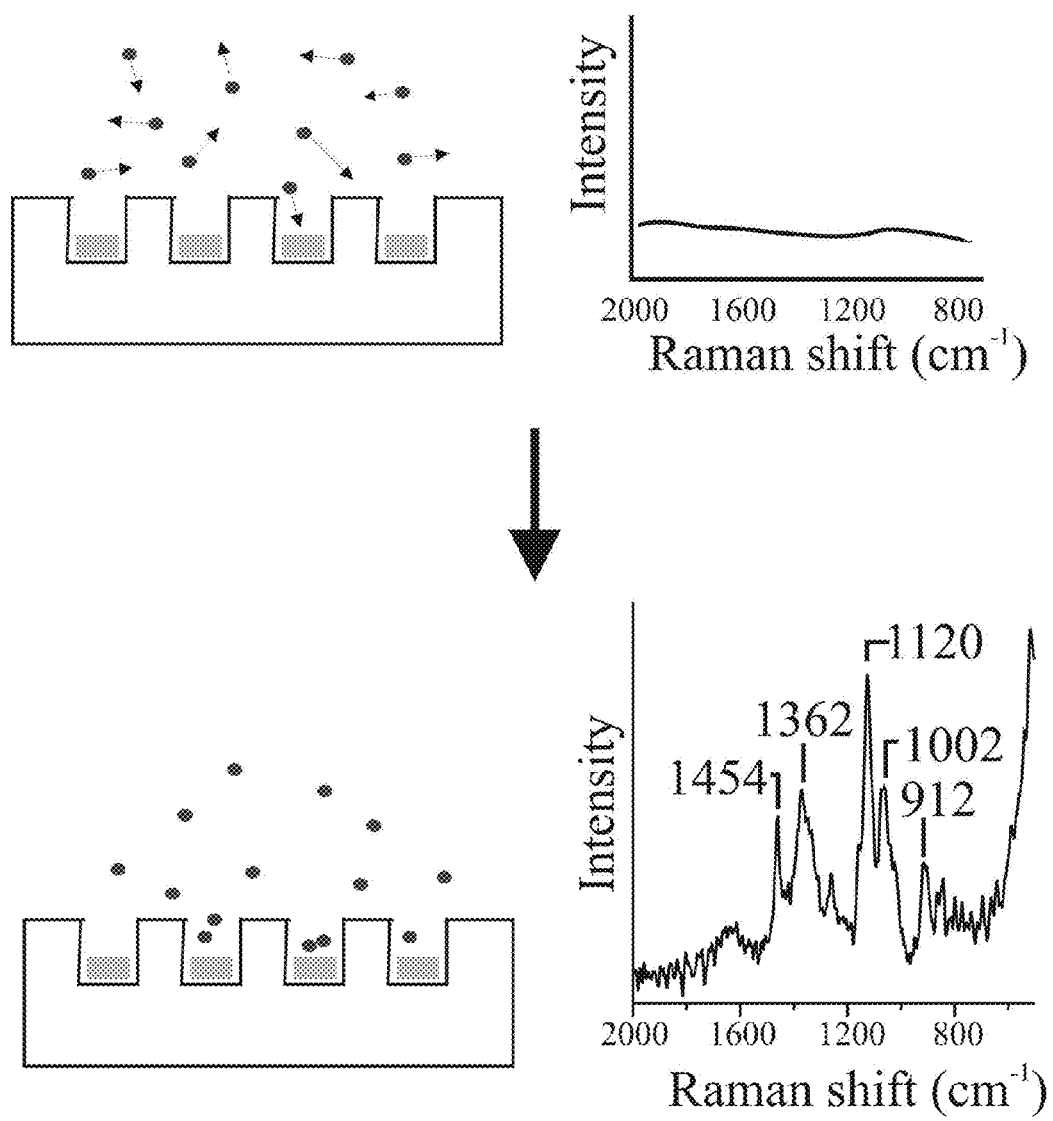
FIG. 4 shows a schematic depicting SERS sensing modality with embedded nanoparticle substrate.
Figure 5:
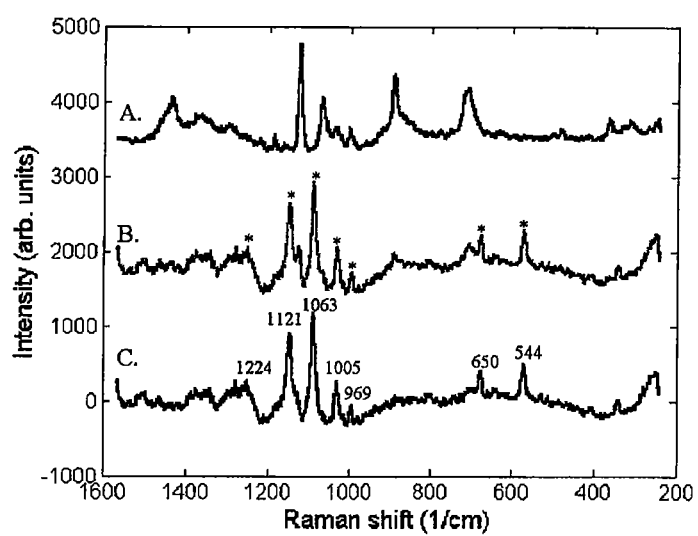
FIG. 5 shows spectrum of 1-DT (FIG. 5A) subtracted from combined 1-DT and glucose spectrum (FIG. 5B) to produce spectrum of glucose (FIG. 5C). *indicates glucose peaks

Many current attempts at in vivo sensing detect the molecule of interest indirectly, based on binding events or pH change. The SERS sensors have the advantage of directly detecting the analytes of interest, allowing facile quantification. A nanowell structure (discussed in more detail below) is used in SERS sensors for both the eye and the skin. Embedded nanoparticle properties (material, size, and spacing) are chosen to optimize the SERS signal resulting from Brownian approach of analyte molecules to the SERS-active substrate (FIG. 4).

In preferred embodiments, the SERS biosensors of the present invention are coated with a noble metal. In some embodiments, the metal is silver. The present invention is not limited to the use of silver. Any noble metal may be utilized, including, but not limited to, gold and platinum. In certain embodiments, a 1 nm layer of titanium or chromium is added to the surface of the particles prior to the silver in order to improve the adhesion of the silver to the surface.

To prolong analyte interaction with the noble metal nanoparticle surface, in some embodiments, a reversibly-binding receptor is used to temporarily bind the analyte to the surface. In the case of glucose, in some embodiments a receptor such as concanavalin A is used as a reversible-binding agent (See e.g., Russell et al., Ana. Chem. 71:3126 [1999]) and/or an alkanethiol, such as 1-decanethiol, is used to form the self-assembled capture layer (Blanco Gomis et al., J. Anal. Chim. Acta 436:173 [2001]; Yang et al., Anal. Chem. 34:1326 [1995]). Other exemplary capture molecules include longer-chained alkanethiols, cyclohexyl mercaptan, glucosamine, boronic acid and mercapto carboxylic acids (e.g., 11-mercaptoundecanoic acid). In other embodiments, apo-glucose oxide is used as the capture molecule.

Alternatively, a self-assembled monolayer (SAM) is formed on the nanoparticle surface to concentrate the analyte of interest near the nanoparticle surface, an adaptation of common high performance liquid chromatography technology. Exemplary SAMs include, but are not limited to, 4-aminothiophenol, L-cystein, 3-mercaptopropionicacid, 11-mercaptoundecanoic acid, 1-hexanethiol, 1-octanethiol, 1-DT, 1-hexadecanethiol, poly-DL-lysine, 3-mercapto-1-propanesulfonic acid, benzenethiol, and cyclohexylmercaptan. In preferred embodiments, the SAM is comprised of straight chain alkanethiols. In some particularly preferred embodiments, the SAM is 1-decanethiol. In other particularly preferred embodiments, the SAM is EG3 (See Example 2). In still further embodiments, the SAM is a thiolated boronic acid. In yet other embodiments, the SAM is polyethylene glycol (PEG) or a thiolated PEG derivative. Preferred SAMs are those that efficiently and reversibly bind analytes but have capture and release kinetic rapid enough to follow fast changes in analyte levels (e.g., physiological glucose levels). In particularly preferred embodiments, the SAM comprises mixed components, for example, DT/MH (decanethiol/mercaptohexanol). In other embodiments, the SAM is modified to substitute a halogen, for example fluorine, for hydrogen.

In some embodiments, a dialysis membrane is utilized to exclude molecules significantly larger than the analyte (e.g., glucose) from contacting the nanoparticle surface. The present invention is not limited to a particular mechanism. Indeed, an understanding of the mechanism is not necessary to understand the present invention. Nonetheless, it is contemplated that the exclusion of large molecules will increase the accuracy and precision of measurement of small molecule analytes such as glucose.

In other embodiments, nanoparticles are coated to prevent the accumulation of interfering proteins on the particle surface. In some embodiments, PEG is immobilized on nanoparticle surfaces to prevent protein fouling. In some embodiments, silica sensor surfaces not coated with silver are PEGylated with silane terminated monomethoxy-PEG and silver coated nanoparticle surfaces are coated with oligoethyleneglycol terminated alkanethiols. In some embodiments, the PEGylated surfaces are analyzed using X-ray photoelectron spectroscopy and secondary ion mass spectra to determine the presence and homogeneity of PEG on surfaces. In some embodiments, protein adhesion to modified surfaces is measured by placing sensors in a culture of fibroblasts for several weeks, removing unattached cells, and counting the number of adhered cells. The effect of suitable anti-fouling coatings on sensor performance can be tested using any suitable method, including, but not limited to, those disclosed in Example 2 below.

While the skin sensor is based on a simple chip implant that can include a $SiO_2$ substrate, the eye sensor is adapted for incorporation into an intraocular by etching nanowells directly into the intraocular lens surface. The choice of excitation wavelength is optimized for data collection in the eye and the skin.

E. Durability of Nanoparticle Arrays

In preferred embodiments, embedded nanoparticles for use in in vivo systems exhibit both optical and physical durability. In experiments conducted during the course of development of the present invention, degradation of the optical signals as the nanoparticles were exposed to many cycles of buffer and solvent rinsing was observed. AFM data indicate that the sharp tips of the triangular nanoparticles are annealed when exposed to these rinse cycles. This change in particle shape causes an uncontrolled shift in the LSPR. In some experiments, the nanoparticles were found to be unintentionally released from the surface into solution. Such release is undesirable for in vivo applications.

In some embodiments, a new nanostructure is used to combat both the uncontrolled shape change and release of nanoparticles. In this nanostructure, the triangular nanoparticles are embedded in $SiO_2$ or polymethylmethacrylate nanowells, effectively immobilizing the nanoparticle and preventing geometric changes while maintaining the advantages of ordered arrays of nanoparticles. This design uses polystyrene or silica nanospheres as a reactive ion etching (RIE) mask. Polystyrene nanospheres are used to create nanowells in the silica substrate for the subcutaneous implant. When $CF_4$ plasma strikes the polystyrene nanospheres, the hydrocarbons are fluorinated. This non-volatile product is not etched away, so the spheres act as an etch stop. Meanwhile, as the $CF_4$ plasma penetrates the pores in the nanosphere mask, volatile $SiF_2$ radicals and $SiF_x$ products are etched away.

Figure 6:
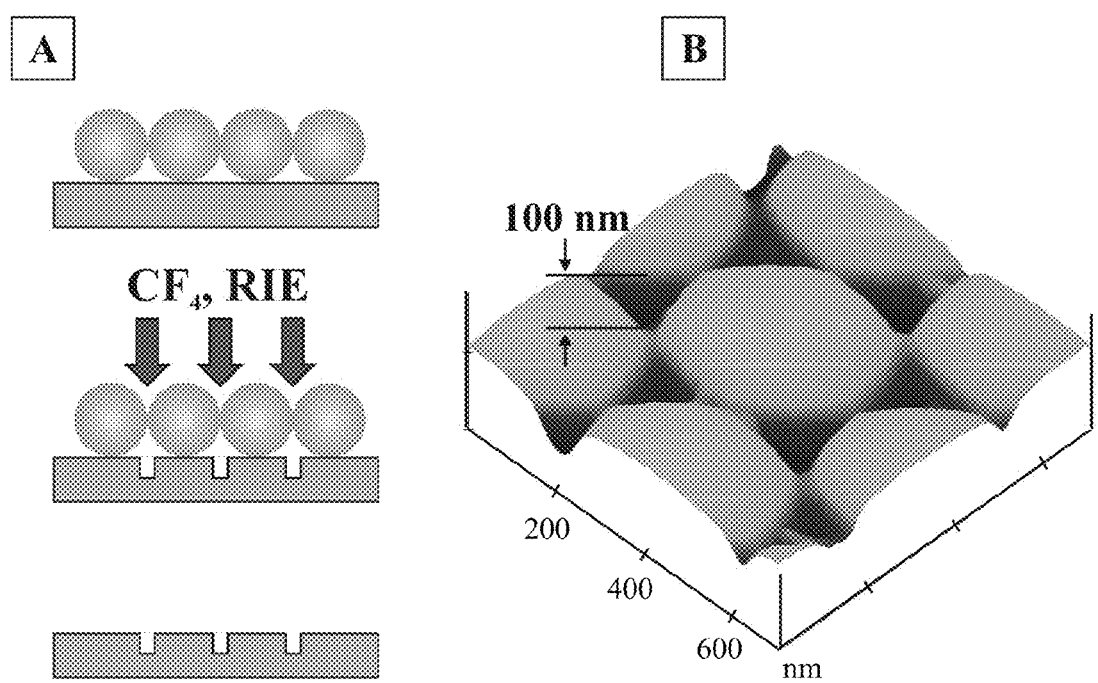
FIG. 6 depicts exemplary steps in nanowell formation.

In some embodiments, silica nanospheres are used to create nanowells in the polymer substrate for the intraocular implant. In this situation, when the $O_2$ plasma strikes the silica nanospheres, only oxygen exchange will occur. Reaction between the $O_2$ plasma and the hydrocarbon intraocular lens produces volatile $CO_x$ products. The resulting structures in both cases are nanowells with a triangular cross-section. Deposition of material through the nanosphere mask after etching embeds nanoparticles within the substrate (FIG. 6). Etched $SiO_2$ samples have been characterized by AFM line scans to show an average etch of 15 nm per minute with 60 mTorr $CF_4$ plasma pressure.

Figure 7:
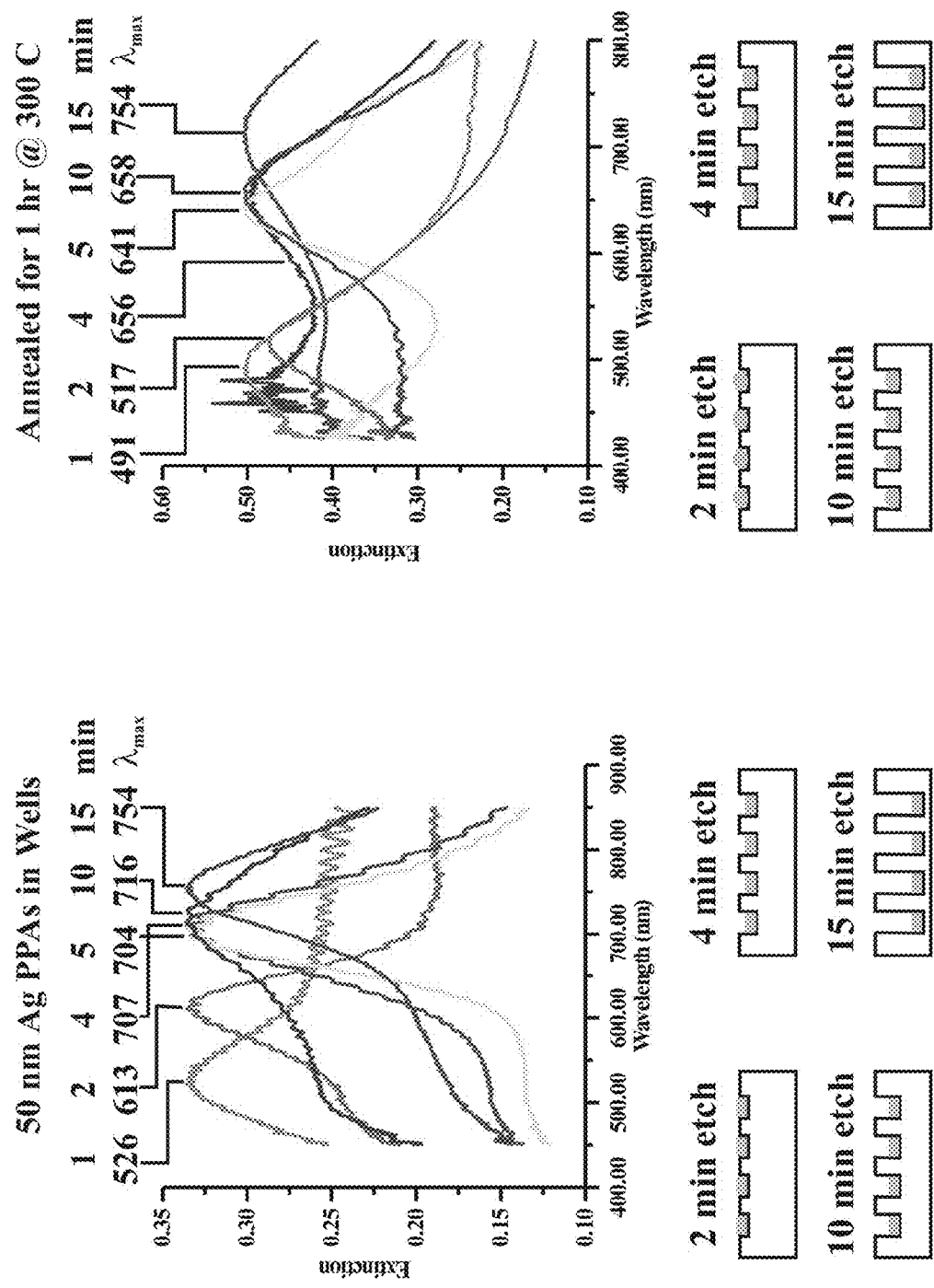
FIG. 7 shows a LSPR spectra of Ag nanoparticles embedded in $SiO_2$ nanowells of varying depths (30 to 300 nm).

Experiments conducted during the course of the present invention (See e.g., Experimental Section below) demonstrated that LSPRs can be measured from embedded nanoparticles and are both measurable and tunable. Seven 400 nm polystyrene diameter nanosphere masks were etched for varied times in a constant 60 mTorr $CF_4$ plasma. The depths of these nanowell structures ranged from 30 nm to 300 nm. Before removing the nanosphere masks, 50 nm of Ag was evaporated onto each sample. The extinction spectra of these embedded nanoparticle structures were then measured (FIG. 7). In order to predict the extinction response of the embedded nanoparticles after being exposed to a physiologically relevant environment, the buried nanoparticles were thermally annealed under vacuum at 300° C. for 1 hour. The general trend for silver nanoparticles was that they become more spherical and increase in height when annealed, yielding a blue shift in the LSPR (FIG. 7).

In other embodiments, nanowells are fabricated on the tip of an optical fiber. In some embodiments, the fiber tip is cleaved and polished prior to use. In some embodiment, a broad reflective dielectric coating is deposited on the tip. In some embodiments, the surface of a fiber optic probe is treated to make the surface clean and hydrophilic (e.g., using 3:1 $H_2SO_4$; 30% $H_2O_2$ at 80° C. for one hour followed by 5:1:1 $H_2O:NH_4OH:30\%$ $H_2O_2$ with sonication for one hour). In some embodiments, a polystyrene nanosphere solution is then drop-coated onto each substrate and allowed to dry. In certain embodiments, the nanosphere coated tip is CF4 plasma reactive ion etched to create wells from 0-300 nm in depth. In some embodiments, silver is vacuum deposited, followed by sonication in ethanol to remove the nanopsheres and leave a tip filled with Ag filled nanowells.

F. Detection and Quantitative Analysis of SERS Signals

In some embodiments, SERS signals are obtained and detected using a laser for excitation. In some embodiments, excitation is at 632.8 nm or 532.0 nm. In preferred embodiments, near infra-red excitation within the "therapeutic window", between 700 and 1200 nm, where absorption by skin is at its minimum is utilized. In some preferred embodiments, the laser power density is below the American National Standards Institute guidelines for human exposure (<2.5 mW cm-2 for 0.25 s, $\lambda$=633 nm, directed at the eye).

Figure 8:
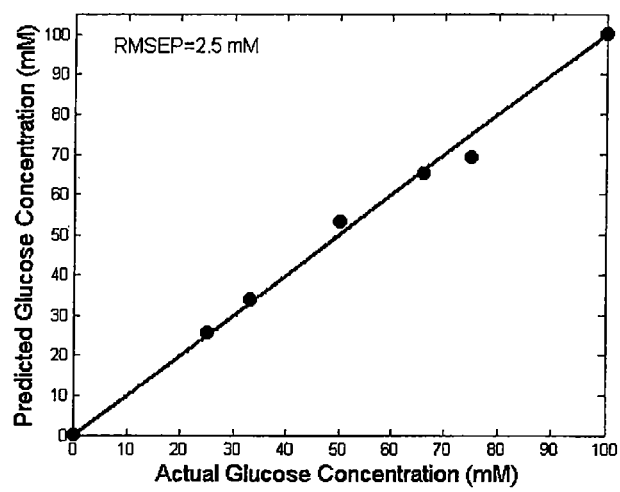
FIG. 8 shows a partial least-squares leave-one-out prediction of glucose concentration versus actual concentration based on measurements made from silver SERS substrate coated with a single monolayer of 1-octanethiol. Primary peak used for prediction is 1121 $cm^{-1}$. The root-mean-squared error of prediction is 2.5 mM.
Figure 13:
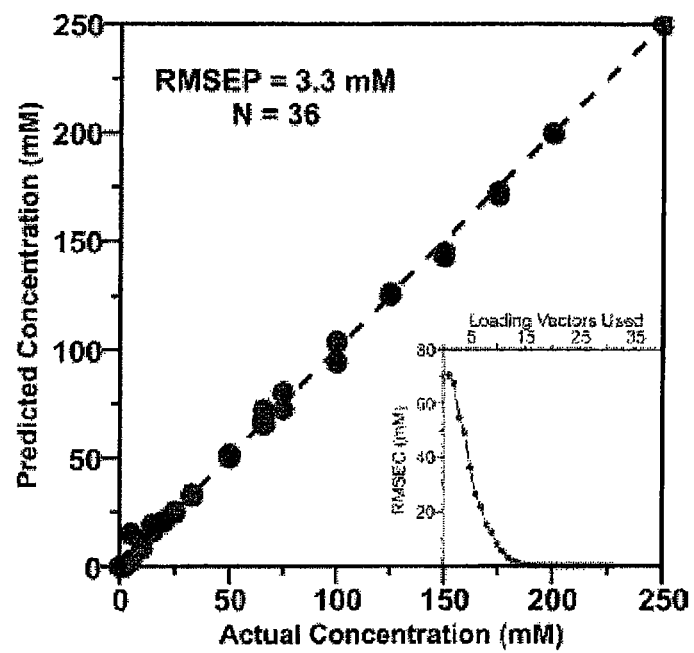
FIG. 13 shows a plot of partial least-squares predicted glucose concentrations versus actual glucose concentrations using leave-on-out cross-validation (21 loading vectors). Each micro-SERS measurement was made under ambient conditions, using $\lambda_{ex}$=632.8 nm (P=4.7 mW, acquisition time (t)=90 sec). The dashed line represents perfect predictions. The inset shows the root-mean-squared error of calibration as a function of number of loading vectors used in the PLS algorithm.
Figure 14:
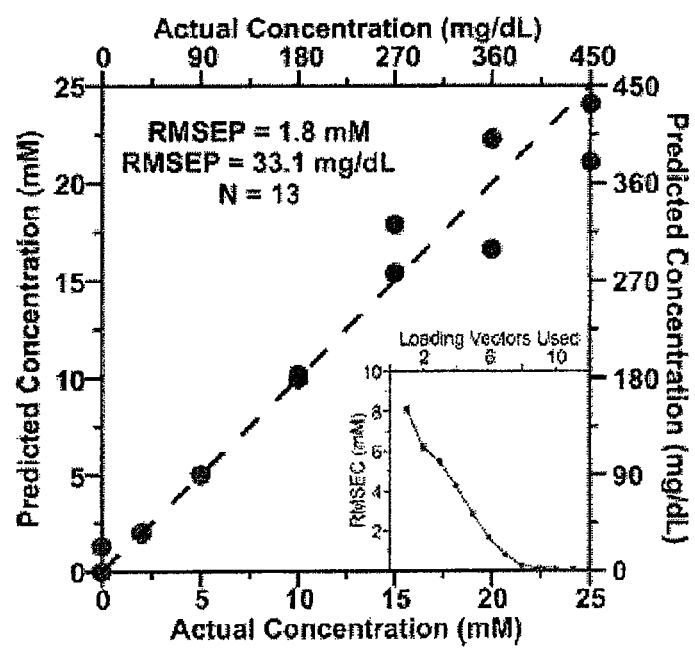
FIG. 14 shows a plot of partial least-squares predicted physiologically-relevant glucose concentrations versus actual glucose concentrations using leave one-out cross-validation (10 loading vectors). Each micro-SERS measurement was made while samples were in an environmental control cell filled with glucose solution, using $\lambda_{ex}$=632.8 nm (P=3.25 mW, acquisition time (t)=30 sec). The dashed line represents perfect predictions. The inset shows the root-mea-squared error of calibration as a function of number of loading vectors used in the PLS algorithm.

In preferred embodiments, both ocular and skin sensors are adapted for quantitative analysis. Manoharan et al. have shown that the normal Raman spectrum of a mixture is a linear combination of the mixture's component spectra, and that there is a linear relationship between signal intensity and chemical concentration (Manoharan et al., J. Photochem. Photobiol. B: Biol. 16:211 [1992]). Experiments conducted during the course of development of the present invention used partial least-squares leave-one-out analysis to show quantitative prediction capability for glucose concentrated by a 1-octanethiol monolayer (FIGS. 8, 13, and 14). Exemplary calibration techniques include, but are not limited to, linear multivariate calibration techniques such as partial-least squares (Geladi et al., Anal. Chim. Acta 185:1 [1986]) and hybrid linear analysis (Berger et al., Anal. Chem. 70:623 [1998]), as well as non-linear techniques such as non-linear partial least-squares and neural networks (Robb et al., Mikrochim. Acta 1:131 [1990]). In some embodiments, an internal standard is incorporated into the sensor device to monitor sensor degradation. Calibration algorithms are optimized for each system and then validated. In preferred embodiments, tissue scattering and absorption are accounted for in subcutaneous measurements.

In some embodiments, the detection system is miniaturized. Miniaturization is preferable for a clinical application in which a subject may wear a detection unit and sensor for continuous monitoring of an analyte. In some embodiments, the spectrophotometer component of the detection system is limited to a narrow, relevant wavelength range in order to decrease the size of the spectrophotometer.

II. Surface-Enhanced Raman Nanobiosensor for Analyte Detection

The following section describes certain preferred embodiments of the invention, but the invention is not limited to these embodiments. In some embodiments, the present invention provides a nanobiosensor for use in the detection of analytes. In some preferred embodiments, the sensor is a surface-enhanced Raman (SERS) nanobiosensor. The in vivo biochemical sensor of the present invention is designed to take advantage of the surface-enhancing properties of noble metallic nanoparticles to acquire Raman spectra from eye (e.g., aqueous humor) or skin (e.g., interstitial fluid, blood), or other organs. Preferred organs for implantation of the sensor are accessible without invasive procedures (e.g., are external) and contain a bodily fluid that is in contact with or exchanges analytes with the entire body.

The surface-enhanced Raman nanobiosensor enables real-time, continuous measurement of multiple analytes (such as glucose, urea, and ascorbate) simultaneously. Another advantage of this technique is that it directly detects the presence of the analytes, rather than relying on an indirect measurement. In some embodiments, the initial placement of the sensor requires surgery, but once in place subsequent measurements are non-invasive.

A. Sensor Fabrication

Figure 9:
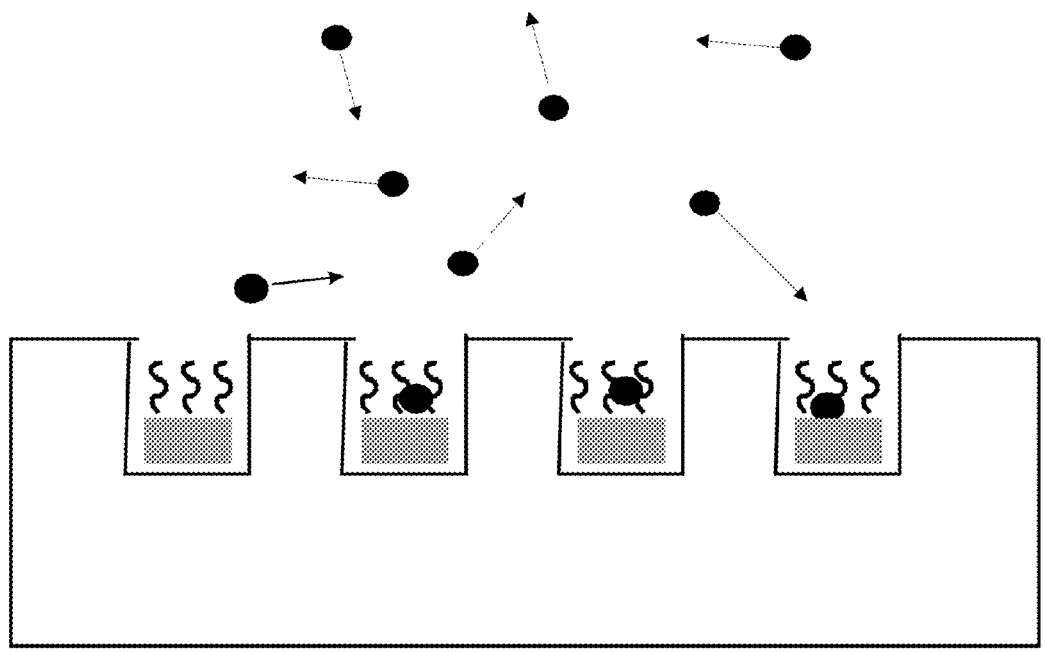
FIG. 9 shows a schematic of nanoparticles embedded in wells and coated with capture layer to increase analyte interaction with the nanoparticles.
Figure 10:
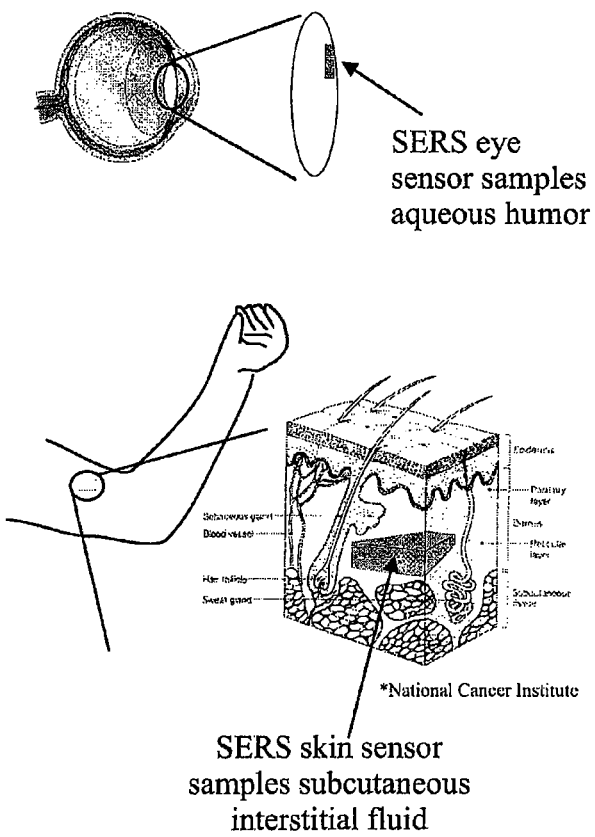
FIG. 10 shows a schematic showing placement of eye and skin implants.

In some embodiments, the sensor is fabricated from a substrate including, but not limited to, polymethacrylate, acrylic, or silicone for the eye and $SiO_2$ for under the skin. In some embodiments, noble metal nanoparticles are deposited into shallow wells in the substrate. In preferred embodiments, the sensor region is only a few millimeters in its longest dimension. In some embodiments, the particles are then coated with a self-assembled monolayer (SAM) to protect them from fouling and to prolong interaction between the analytes of interest and the surface (FIG. 9). In some embodiments, reversibly-binding receptors are incorporated into this SAM. The sensor is implanted either under the skin or used to replace the intraocular lens (FIG. 10). To detect surface-enhanced Raman signals from the sensor, delivery and collection optics as well as a laser source, an optical filter, and a detector are used. In some embodiments, the delivery and collection optics (as well as filters) are incorporated into a fiber optic probe, which is connected to the laser and detector.

B. Mixed Partition Layers Enables Real-Time Glucose Sensing by Surface Enhanced Raman Spectroscopy in Plasma In some embodiments, the present invention provides a composition comprising a biosensor comprising a substrate, and a plurality of nanobiosensors adherent to the substrate, comprising: a plurality of nanospheres; a metal film over the nanospheres (MFON); and a self-assembled partition layer formed on the surface of the metal film over the nanospheres comprising at least two compounds, wherein the nanobiosensors are configured for the quantitative detection of an analyte such that the spectrum of a surface-enhanced Raman signal detected from the plurality of nanobiosensors in the presence of the analyte is correlated with the concentration of the analyte in a medium. Experiments conducted during the course of development of the present invention led to the discovery of a mixed decanethiol (DT) partition layer with improved properties that has been developed for glucose sensing by surface-enhanced Raman spectroscopy (See Experimental Example 4, below). DT is hydrophobic and not compatible with an aqueous environment. The mixed partition layer based on two commercially available components, decanethiol (DT) and mercaptohexanol (MH) exhibits (1) temporal stability on an AgFON surface of the nanobiosensor, (2) rapid (less than one min), reversible partitioning and departitioning of glucose on a DT/MH-functionalized AgFON surface, (3) quantitative detection of glucose in aqueous solution with interfering analytes and in bovine plasma over the physiological and pathological concentration ranges, and (4) real-time kinetics of glucose partitioning and departitioning. Moreover, the DT/MH-functionalized surface is simple to assemble and to control.

While the present invention is not limited to a particular mechanism of action, and an understanding of the mechanism is not necessary to practice the present invention, it is nonetheless contemplated that on space filling models the hydroxyl-terminated chains form hydrophilic pockets, thus partitioning glucose closer to the SERS-active surface. In turn, the DT/MH SAM has dual hydrophobic/hydrophilic functionality thereby excluding non-target molecules such as proteins that could give rise to spectral congestion. This property facilitates detection by simplifying the composition of the solution at the surface, while the SERS spectra provide a vibrational "fingerprint" that is unique to each molecule.

C. Uses of Sensors

In some embodiments, the eye implant is a modified intraocular lenses commonly used in lens replacements when cataracts occur. The noble metal nanoparticles are incorporated into a small portion of these lenses to form the sensor.

In some embodiments, for skin implant sensor fabrication, the noble metal nanoparticles are deposited in shallow wells in a chip (e.g., only a few millimeters in its longest dimension) composed of $SiO_2$.

In some embodiments, the surface-enhanced Raman nanobiosensors of the present invention enable faster, easier, and continuous measurement glucose levels for diabetics. In other embodiments, the nanobiosensors are used in the measurement of previously unmonitored analytes critical in other diseases. Continuous measurements of blood glucose levels open the door to implanted insulin pumps. In some embodiments, a SERS nanobiosensor is used for monitoring drug-delivery in many situations, enabling tighter control over drug administration.

The methods of the present invention are not limited to the detection of glucose. Previously, SERS has been used to detect a wide variety of analytes present at low concentrations, including, but not limited to, pollutants (Weissenbacher et al., J. Mol. Struct. 410-411:539 [1997]), explosives (McHugh et al., Chem. Commun. 580:-581 [2002]; Sylvia et al., Anal. Chem. 72:5834 [2000]), chemical warfare agents (Taranenko et al., J. Raman Spec. 27:379 [1996]), and DNA (Vo Dinh et al., J. Raman Spec. 30:785 [1999]). The methods of the present invention are thus applicable to the in vivo detection of exposure (e.g., monitoring) of individuals exposed to such agents.

D. In Vivo Measurement of Glucose Concentration by Surface-Enhanced Raman Spectroscopy on Chemically Modified Metal Film Over Nanosphere Substrates In some embodiments, the present invention provides a method for detection of an analyte in vivo with the biosensor of the present invention implanted in a subject. In experiments conducted during the course of development of the present invention SERS was used to obtain in vivo quantitative glucose measurements from an animal model (See Experimental Example 5, below). Silver film over nanosphere (AgFON) substrates were functionalized with a two component self-assembled monolayer (SAM) (See Experimental Example 4, below), and the biosensor of the present invention was subcutaneously implanted in a Sprague-Dawley rat such that the glucose concentration of the interstitial fluid could be spectroscopically addressed through an optical window.

In vivo applications of SERS confront a number of challenges. Analytes of interest must be in close physical proximity to (~1-2 nm), or adsorbed on, a roughened metal surface. In turn, the complexity and structural similarity of many molecules (e.g., proteins) may yield SERS spectra that are difficult to interpret. Moreover, placement of the SERS active surface in living systems must avoid damage to either the host or the surface. While colloid-based substrates may be difficult to introduce into cells and can coalesce in the extracellular space, solid substrates are more robust, but require surgical implantation. Additional problems may become apparent after the substrate is surgically implanted and surrounded by a biological medium. For example, there may be little of no control over which species adsorb, perhaps irreversibly, to the SERS active surface. This condition potentially creates undesired spectral noise from non-target molecules, while simultaneously blocking the access of the desired species, lowering the possible signal. Cellular and in vivo environments may be awash with a multitude of interfering molecules whose presence and concentration are in a constant state of flux. Similarly, the concentration of the target analyte itself may be invariably changing. These challenges are compounded in vivo by host immune responses, clotting factors, and the concentration of target species in the extracellular matrix. In aggregate, these factors may contribute to surface contamination and cause unwanted effects.

As shown in Experimental Example 5, the present invention addresses and surmounts these challenges. In experiments conducted during the course of development of the present invention, a technique that addresses the critical problems previously limiting the use of SERS to glucose measurements, particularly in vivo, has been developed. Advances include the development of stable and strongly enhancing SERS active surfaces, and the chemical functionalization of those surfaces with self-assembled monolayers (SAMs). (See Experimental Examples 1, 2 and 4, below).

While the present invention is not limited to a particular mechanism of action, and an understanding of the mechanism is not necessary to practice the present invention, it is nonetheless contemplated that the multiple roles performed by SAMs in the in vivo detection system include limiting fouling, providing an internal standard, segregating classes of interferants from the detection surface, and amplifying the analyte signal. Stability of the SERS signal, and substrate stability itself is primarily determined by the material properties of the enhancing substrate. (Stuart, et al., The Analyst [2005] (in press); McFarland et al., Phys. Chem. B. 109: 11279 [2005]). Experiments were conducted during the course of development of the present invention that verified the parameters required to optimize the plasmonic properties of the FON type substrates. Although the FON variant of NSL is intrinsically less enhancing (EF=$10^6$) than other NSL varieties ($10^8$), FONs provide higher overall SERS signals. While the present invention is not limited to a particular mechanism of action, and an understanding of the mechanism is not necessary to practice the present invention, it is nonetheless contemplated that this is because the total signal is related to both the SERS EF and the number of analyte molecules probed, which is quite high for FONs because of their relatively large viable surface area. The high radius of curvature imparted by the underlying nanospheres prevents annealing or loss of the nanoscale roughness features that give rise to SERS. Hence, the use of SAM functionalized substrates allows the present invention to overcome many of the in vivo the hurdles cited above (Lyandres et al., Analytical Chemistry 77:6134 [1005]; Sulk et al., Journal of Raman Spectroscopy 30:853 [1999]), thereby providing a minimally invasive, real-time continuous, reusable, quantitative SERS glucose sensor as a candidate for implantable sensing.

III. Kits

In some embodiments, the present invention provides kits and systems for use in monitoring the level of an analyte in an individual. In some embodiments, the kits are kits for home use by a subject (e.g., a subject with diabetes). For example, in some embodiments, a sensor is implanted in the skin or the eye of a subject (e.g., by a medical professional) and the subject is provided with a device for monitoring levels of analyte (e.g., the subject places the device near the sensor and the device reads-out glucose levels). The subject can then use this information to maintain better control of blood glucose levels and avoid complications of the disease. In some embodiments, the sensor is used extra-corporeally by introducing a biological sample (e.g., blood) to the device.

In other embodiments, the present invention provides kits for use by medical professionals. For example, in some embodiments, the present invention provides kits for monitoring military personnel in a war situation where they may be exposed to toxins. The sensors are implanted prior to potential exposure (e.g., prior to departing for active duty). Personnel are then monitored by medical professionals using a detection device.

In still further embodiments, the present device is used at home or by a medical professional to monitor exposure to pesticides (e.g., in agricultural workers). The workers receive a sensor and are then monitored using a detection device.

In yet other embodiments, the present invention provides systems comprising nanobiosensors and detection devices. For example, in some embodiments, the systems are combined with an insulin delivery device (e.g., an insulin pump) for use as an artificial pancreas. Such a device finds use in the treatment of individuals with diabetes who require regular insulin doses. In some embodiments, the detection device and pump are external (e.g., combined into one unit). The device takes readings from a sensor (e.g., implanted in the skin near the device), calculates blood glucose concentration, and administers an appropriate level of insulin. In other embodiments, the entire system is internal (e.g., implanted underneath the skin or located in the abdominal cavity). In some embodiments, the entire system is a single unit comprising a sensor, a detection device, and an insulin delivery device.

EXPERIMENTAL

The following examples serve to illustrate certain preferred embodiments and aspects of the present invention and are not to be construed as limiting the scope thereof.

Example 1

Optimization of SAMs for Biosensors

This Example describes the characterization of glucose sensing biosensors comprising a variety of SAMs.

A. Materials

Ag (99.99%, 0.04" diameter) was purchased from D. F. Goldsmith (Evanston, Ill.). Glass substrates were 18 mm diameter, No. 2 coverslips from Fisher Scientific (Fairlawn, Va.). Pretreatment of substrates required H2SO4, H2O2, and NH4OH, all purchased from Fisher Scientific (Fairlawn, Va.). Surfactant-free white carboxyl-substituted polystyrene latex nanospheres with diameters of 390±19.5 nm were obtained from Duke Scientific Corporation (Palo Alto, Calif.). Tungsten vapor deposition boats were purchased from R. D. Mathis (Long Beach, Calif.). 4-aminothiophenol (90%), L-cysteine (97%), 3-mercaptoproprionic acid (99+%), 11-mercaptoundecanoic acid (95%), 1-hexanethiol (95%), 1-octanethiol (98%), 1-DT (96%), 1-hexadecanethiol (92%), 3-mercapto-1-propanesulfonic acid (Na+ salt, 90%), benzenethiol (99+%), cyclohexylmercaptan (97%), α-D-Glucose (ACS Reagent Grade) were purchased from Aldrich (Milwaukee, Wis.) and used as received. Poly-DL-lysine hydrobromide was purchased from Sigma (St. Louis, Mo.). Ethanol was purchased from Pharmco (Brookfield, Conn.). For all steps of substrate and solution preparation, ultrapure water (18.2 MΩcm-1) from a Millipore academic system (Marlborough, Mass.) was used.

AgFON Fabrication and Incubation Procedure.

Borosilicate glass substrates were pretreated in two steps (1) pianha etch, 3:1 $H_2SO_4$: 30% $H_2O_2$ at 80° C. for 1 hr, was used to clean the substrate, and (2) base treatment, 5:1:1 $H_2O:NH_4OH$: 30% $H_2O_2$ with sonication for 1 hour, was used to render the surface hydrophilic. Approximately 2 µL of undiluted nanosphere solution (4% solids) were drop coated onto each substrate and allowed to dry in ambient conditions. The metal films were deposited in a modified Consolidated Vacuum Corporation vapor deposition system (Hulteen et al., J. Vac. Sci. Technol. A 13:1553 [1995]) with a base pressure of $10^{-7}$ torr. The mass thickness of Ag in all cases was 200 nm and deposition rates for each film (1 nm/sec) were measured using a Leybold Inficon XTM/2 quartz-crystal microbalance (QCM)(East Syracuse, N.Y.). Fresh AgFON samples were incubated in 1 mM solutions of the partition layer self-assembled monolayers (SAMs) in ethanol for >12 hours before being exposed to glucose solutions of the desired concentration. Each sample was dosed in a separate vial. Glucose solutions ranged in concentration from 0-250 mM in 80% ethanol:20% water.

Micro-SERS Apparatus

Spatially-resolved SER spectra were measured using a modified Nikon Optiphot (Frier Company, Huntley, Ill.) confocal microscope with a 20× objective in backscattering geometry. The laser light from a Coherent (Santa Clara, Calif.) model 590 dye laser operating at $\lambda_{ex}$=632.8 nm or a Spectra-Physics (Moutainview, Calif.) model Millenia Vs laser operating at $\lambda_{ex}$=532.0 nm was coupled into a 200 µm core diameter fiber using a Thorlabs (Newton, N.J.) fiber launch. Appropriate Edmund Scientific (Barrington, N.J.) interference filters and Kaiser (Ann Arbor, Mich.) holographic notch filters were placed in the beam path. The backscattered light was collected by an output fiber optic coupled to an Acton (Acton, Mass.) VM-505 monochromator (entrance slit set at 250 µm) with a Roper Scientific (Trenton, N.J.) Spec-10:400B liquid N2-cooled CCD detector.

Chemometrics Method

All data processing was performed using MATLAB (MathWorks, Inc., Natick, Mass.) and PLS_Toolbox (Eigenvector Research, Inc., Manson, Wash.). Prior to analysis, cosmic rays were removed from the spectra using a derivative filter and the slowly-varying background, commonly seen in SERS experiments, was removed by subtracting a fourth-order polynomial. The data was then mean-centered. Data analysis was performed using partial least squares (PLS) leave-one-out (LOO) analysis. PLS was chosen from among the many chemometric techniques available because it only requires knowledge of the concentrations of the analyte of interest during calibration (Geladi et al., Anal. Chim. Acta. 185:1 [1986]; Haaland et al., Anal. Chem. 60:1193 [1988]). Other techniques, such as classical least-squares require knowledge of all of the chemicals present in the sample. Although the precise amount of glucose added to each sample is known in the presented experiments, the knowledge of the other chemicals in the background (e.g. polystyrene from substrate preparation or impurities in the partition layers) was not known.

Whenever a chemometric technique is used, proper validation is preferred to aid in obtaining meaningful results. Usually two separate data sets are used, one for calibration and one for validation. Because of the limited number of samples in the data set, LOO was chosen as the cross-validation technique (Martens et al., Multivariate Calibration; Wiley:Chichester, 1989). In LOO analysis, one sample at a time is left out of the calibration set. The PLS model is developed using the remaining data and then applied to the lone sample. The predicted concentration of this sample is then compared to the actual concentration and used to evaluate the quality of the model. The process is then repeated, leaving each sample out, one at a time, to build up a set of validation results. LOO cross-validation enables evaluation of a new technique despite a relatively small data set. Prediction error in the calibration and validation sets was determined by calculating the root-mean-squared error of prediction (RMSEP), $$RMSEP = \sqrt{\frac{(conc_1 - pred_1)^2 + (conc_2 - pred_2)^2 + \ldots + (conc_n - pred_n)^2}{n}} \quad (1)$$

In this equation, conc represents the actual concentration of a sample, pred represents the predicted concentration for that sample, and n is the total number of samples. The choice of the number of loading vectors to use in the PLS results discussed here was determined by the number of loading vectors needed for the root-mean-squared error of calibration (RMSEC) to stabilize at a minimum value.

B. Results

Figure 12:
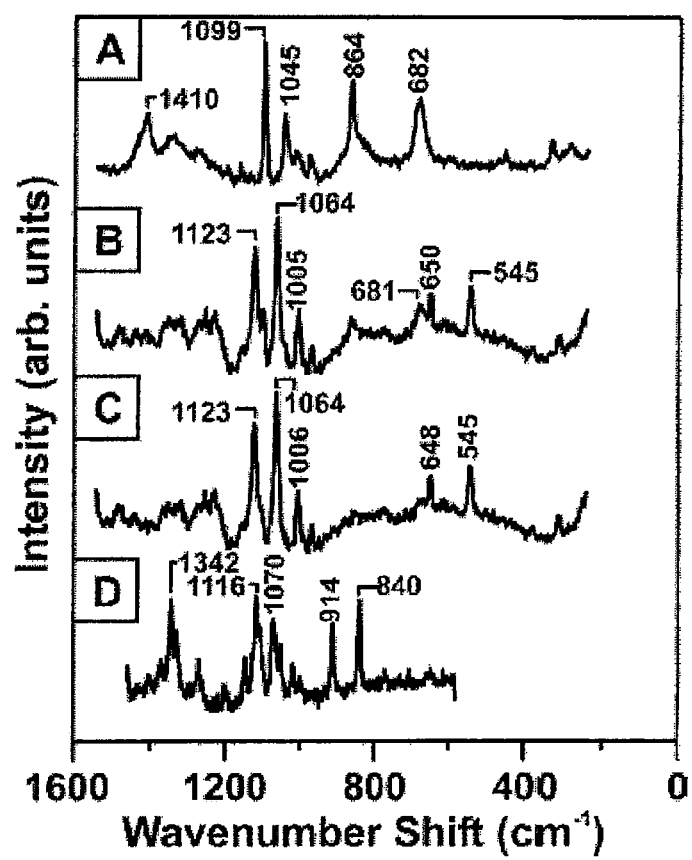
FIG. 12 shows spectra used in quantitative analysis.

Several SAMs were tested to determine their effectiveness as a partition layer. The twelve SAMs tested were 4-aminothiophenol, L-cystein, 3-mercaptopropionicacid, 11-mercaptoundecanoic acid, 1-hexanethiol, 1-octanethiol, 1-DT, 1-hexadecanethiol, poly-DL-lysine, 3-mercapto-1-propanesulfonic acid, benzenethiol, and cyclohexylmercaptan. Of these, only the straight chain alkanethiols were found to be effective partition layers, especially 1-DT (which forms a monolayer on silver ~1.9 nm thick) (Walczak et al., J. Am. Chem. Soc. 113:2370 [1991]). 1-DT almost completely fills the theoretical first decay length of the electromagnetic fields from the SERS substrate (Schatz et al., In Handbook of Vibrational Spectroscopy; Chalmers, J. M., Griffiths, P. R. Eds.; John Wiley & Sons: Chichester, UK, 2002; Vol. 1 pp 775-784. FIG. 12 shows example spectra from the different stages of assembly of the glucose/1-DT/AgFON surface. FIG. 12A shows the SER spectrum of 1-DT on a AgFON surface. After 10 minutes incubation in 100 mM glucose solution, the SER spectrum in FIG. 12B was observed. This spectrum is the superposition of the SER spectra for the partition layer and glucose. FIG. 12B shows vibrational features from both the analyte glucose (1123 and 1064 cm-1) and 1-DT (1099, 864, and 681 cm-1) constituents. The SERS difference spectrum resulting from subtraction of spectrum 12A from spectrum 12B is shown in FIG. 12C. The difference spectrum can be compared directly to the normal Raman spectrum of crystalline glucose shown in FIG. 12D. The vibrational bands seen at 914 cm-1 and 840 cm-1 in the crystalline glucose spectrum (FIG. 12D) are not observed in the spectra shown in FIGS. 12B and 12C because these bands are strongest in crystalline glucose; this phenomenon has been previously observed (Mrozek et al., J. Anal. Chem. 74:4069 [2002]).

In the initial quantitative experiment, AgFON surfaces with a monolayer of 1-DT were incubated for ten minutes in a solution containing glucose concentrations ranging from 0-250 mM. SER spectra were then measured from each sample using $\lambda_{ex}$=632.8 nm ($P_{laser}$=4.7 mW, acquisition time (t)=90 s). In all 36 cases, the measurements were made on samples in dry, ambient conditions. Upon performing LOO-PLS analysis, 21 loading vectors were found to minimize the root-mean-squared error of calibration (RMSEC), see inset of FIG. 13. The resulting cross-validated glucose concentration predictions, using 21 loading vectors, can be seen in FIG. 13.

The corresponding error of prediction is 3.3 mM. This result was repeated with multiple, similar data sets. While quantitative SERS detection is demonstrated in the aforementioned data set, a clinically-relevant concentration range is preferred. Accordingly, AgFONs with a monolayer of 1-DT were incubated for an hour in glucose solutions diluted by a factor of 10 (0-25 mM, 0-450 mg/dL). SER spectra were then measured from each sample using $\lambda_{ex}$=632.8 nm ($P_{laser}$=3.25 mW, acquisition time (t)=30 s). In all 13 cases, the measurements were made on samples in a simple environmentally controlled cell, bathed in the corresponding glucose solution. Upon performing LOO-PLS analysis, 10 loading vectors were found to minimize the root-mean-squared error of calibration (RMSEC), see inset of FIG. 14. The resulting cross-validated glucose concentration predictions, using 10 loading vectors, can be seen in FIG. 14. The corresponding error of prediction is 1.8 mM. Fewer loading vectors and a lower RMSEP in the smaller concentration range experiment may be attributable to the onset of a non-linear signal versus glucose concentration relationship (i.e. the non-linear portion of the partition isotherm) as higher concentrations are partitioned.

Figure 15:
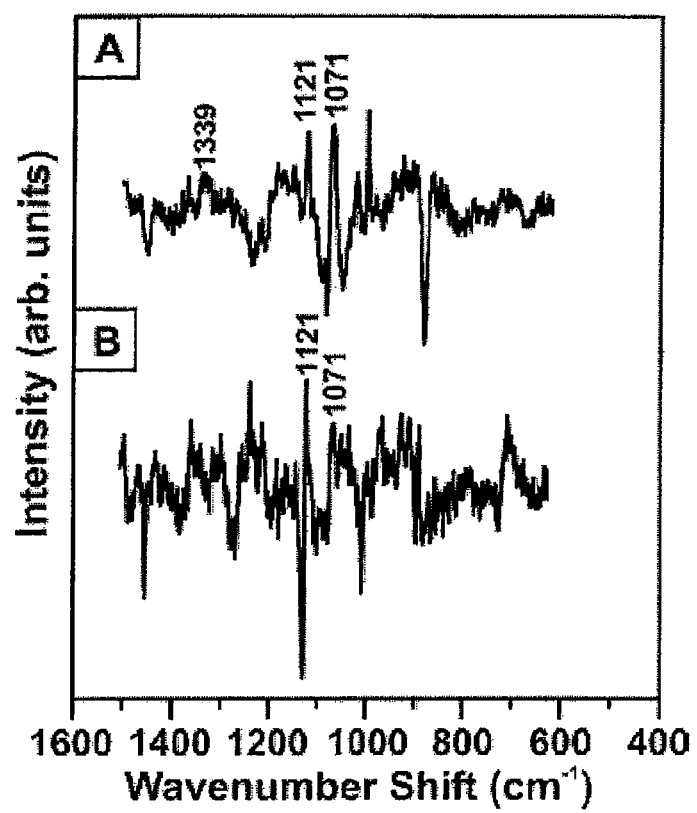
FIG. 15 shows calibration vectors used to produce predictions shown in FIGS. 13, and 14, respectively.

In the calibration vectors (FIGS. 15A and 15B) used to generate the prediction plots seen in FIGS. 13 and 14, the characteristic vibrational bands of glucose are clearly visible at 1121 $cm^{-1}$ and 1071 $cm^{-1}$. These calibration vectors represent the portions of glucose that do not overlap with bands of the partition layer or analytes present in the background. Accordingly, some glucose features are absent, while others represent the portion of the glucose band not overlapping with those bands of 1-DT.

In conclusion, the first systematic detection of glucose using SERS is described. The SERS bands observed clearly at 1123 $cm^{-1}$ and 1064 $cm^{-1}$ demonstrate the vibrational features of glucose in solution. The adsorption problem has been circumvented by partitioning glucose into an alkanethiol monolayer adsorbed on the silver surface thereby pre-concentrating it within the zone of electromagnetic field enhancement. Of the 12 partition layers studied, only straight chain alkanethiols were found to be effective. Consequently, 1-DT was chosen as the partition layer for all the studies.

Two data sets are presented to support the quantitative detection of glucose using SERS. The first probes the quantitative prediction of glucose over a large concentration range (0-250 mM), demonstrating a root-mean-squared error of prediction (RMSEP) of 3.3 mM. The second covers the clinically-relevant concentration range (0-25 mM/0-450 mg/dL), performed in a liquid environment with short (viz. 30 second) data acquisition times. This data set is effectively treated using LOO-PLS and displays a RMSEP of 1.8 mM (33.1 mg/dL), near that desired for medical applications. The calibration vectors derived in both experiments using the PLS algorithm show the characteristic vibrational features of glucose.

Example 2

Biosensors Utilizing EG3 Monolayers

This Example describes the characterization of glucose-sensing biosensors comprising EG3 self assembled monolayers.
A. Methods
Materials All the chemicals were of reagent grade or better, and used as purchased. Ag wire (99.99%, 0.04 inch diameter) was purchased from D. F. Goldsmith (Evanston, Ill.). Oxygen-free high conductivity copper was obtained from McMaster-Carr (Chicago, Ill.) and cut into 18-mm-diameter discs. $CH_3CH_2OH$, $H_2O_2$, and $NH_4OH$ were purchased from Fisher Scientific (Fairlawn, Va.). Surfactant-free white carboxyl-substituted latex polystyrene nanosphere suspensions (390±19.5 nm diameter, 4% solid) were acquired from Duke Scientific Corporation (Palo Alto, Calif.). Tungsten vapor deposition boats were purchased from R. D. Mathis (Long Beach, Calif.). For substrate and solution preparations, ultra-pure water (18.2 MΩcm-1) from a Millipore academic system (Marlborough, Mass.) was used. Bovine serum albumin and saline were obtained from Sigma (St. Louis, Mo.). The disposable filters with 0.45-µm-pore size were acquired from Gelman Sciences (Ann Arbor, Mich.). (1-Mercaptoundeca-11-yl)tri(ethylene glycol) ($HS(CH_2)_{11}(OCH_2CH_2)_3OH$, EG3) was synthesized (Palegrosdemange et al., J. Am. Chem. Soc. 113:12-20 [1991]) and donated by the Mrksich group at the University of Chicago (Hodneland et al., Proc. Natl. Acad. Sci. 99:5048 [2002]).
AgFON Fabrication and Incubation Procedure AgFON substrates were used because of their stable SERS activity in electrochemical ultrahigh vacuum (Dick et al., J. Phys. Chem. B106:853 [2002]; Dick et al., J. Phys. Chem. B 104:11752 [2000]; Litorja et al., J. Phys. Chem. B 105: 6907 [2001]) and ambient experiments (Shafer-Peltier et al., J. Am. Chem. Soc. 125: 588 [2003]). In this work, AgFONs were fabricated on copper substrates. The copper substrates were cleaned by sonicating in 10:1:1 $H_2O$:30% $H_2O_2$:$NH_4OH$. Approximately 12 µL of nanosphere solution was drop-coated onto a clean copper substrate and allowed to dry at room temperature. Then, 200-nm-thick Ag films were deposited onto and through the nanosphere mask using a modified Consolidated Vacuum Corporation vapor deposition system (base pressure 10-7 Torr) (Hulteen et al., J. Vac. Sci. Technol. A 13:1553 [1995]). The mass thickness and deposition rate (1 nm/sec) of the Ag metal were measured by a Leybold Inficon XTM/2 quartz-crystal microbalance (East Syracuse, N.Y.). AgFON substrates were first incubated in 1 mM EG3 in ethanol for more than 12 hours. Then, the EG3-modified substrates were mounted into a small volume flow cell and exposed to glucose solutions for 10 minutes to ensure complete partitioning of the glucose into the EG3 monolayer.
Surface-Enhanced Raman Scattering Spectroscopy A Spectra-Physics model 120 HeNe laser was used to produce the 632.8 nm excitation wavelength ($\lambda$ex); the laser spot size was less than 2 mm in diameter. The SERS measurement system includes an interference filter (Edmund Scientific, Barrington, N.J.), a holographic notch filter (Kaiser Optical Systems, Ann Arbor, Mich.), a model VM-505 single-grating monochromator with the entrance slit set at 100 µm (Acton Research Corp., Acton, Mass.), and a liquid $N_2$-cooled CCD detector (Roper Scientific, Trenton, N.J.). The small volume flow cell (Malinsky et al., J. Am. Chem. Soc. 123:1471 [2001]) was used to control the external environment of AgFON surfaces throughout the SERS experiment.
Chemometrics Method All data processing was performed using MATLAB (MathWorks, Inc., Natick, Mass.) and PLS_Toolbox (Eigenvector Research, Inc., Manson, Wash.). Prior to analysis, cosmic rays were removed from the spectra using a derivative filter. The slowly-varying background, commonly seen in SERS experiments, was also removed by subtracting a fourth-order polynomial. Data analysis was performed using partial least-squares (PLS) leave-one-out (LOO) analysis.
B. Results Significant progress has been made toward achieving a real-time, non-invasive, biocompatible SERS glucose sensor.

Figure 16:
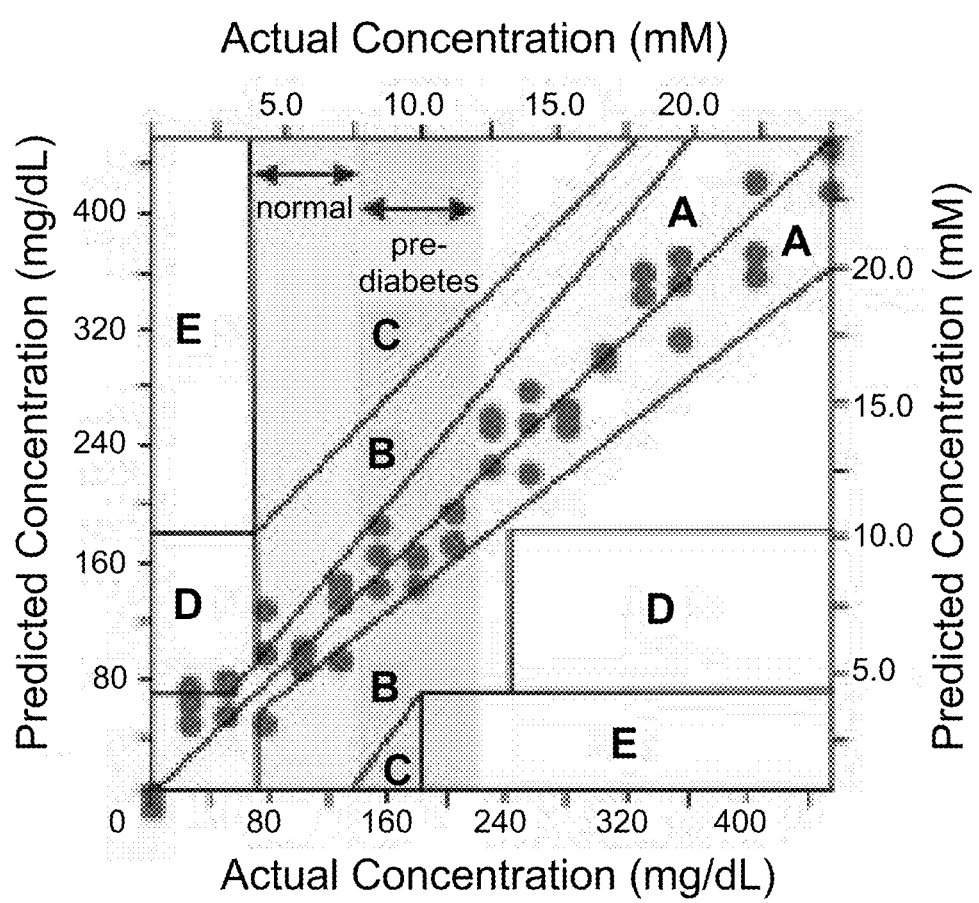
FIG. 16 shows a Clarke error grid of glucose detection by nanobiosensors of some embodiments of the present invention.

In previous work (See Example 1), decanethiol was used as a partition layer for glucose, but the required sensor characteristics of temporal stability, reversibility, and biocompatibility were not studied in detail. Herein, EG3 was chosen as a partition layer because of its biocompatibility and hydrophilic properties, progressing toward the long-term goal of fabricating an implantable glucose sensor. The EG3-modified AgFON substrate was exposed to various concentrations of glucose under physiological conditions, promoting preconcentration of glucose near the AgFON surface. After data analysis using LOO-PLS, the results are presented in a Clarke error grid (FIG. 16). Clarke and coworkers established the Clarke error grid as a metric for evaluating glucose sensor efficacy in the clinical concentration range (Clarke et al., Diabetes Care 10:622 [1987]). The Clarke error grid is divided into five major zones: zone A predictions lead to clinically correct treatment decisions; zone B predictions lead to benign errors or no treatment; zone C predictions lead to overcorrecting acceptable blood glucose concentrations; zone D predictions lead to dangerous failure to detect and treat; and zone E predictions lead to further aggravating abnormal glucose levels.

Quantitative Study of Glucose Using an EG3 Partition Layer

A viable glucose biosensor should be capable of detecting 0-450 mg/dL (0-25 mM) glucose under physiological conditions. Each EG3-modified AgFON sample was incubated for 10 minutes in a pH=7.4 saline solution containing glucose concentrations from 0-450 mg/dL (0-25 mM). The samples were placed in an environmental control flow cell under saline, and SERS spectra were then measured ($\lambda$ex=632.8 nm, Plaser=2.5 mW, acquisition time (t)=30 s). After spectral normalization using EG3 peak intensities, the SERS spectra were analyzed with the LOO-PLS method.

In the data presented in FIG. 16, five loading vectors were found to minimize the root-mean-squared error of cross validation (RMSECV). The resulting cross-validated glucose concentration predictions are presented in the Clarke error grid (FIG. 16). The EG3-modified AgFON sensor quantitatively detects glucose in the physiological range with a corresponding RMSECV of 82 mg/dL (4.5 mM). In FIG. 16, 94% of the predictions fall in zones A and B, while a few data points overlap in zone D within the hypoglycemic area (<70 mg/dL, <3.9 mM). The prediction error of 82 mg/dL (4.5 mM) can be partially attributed to variation of the SERS enhancement factor on different AgFON samples. The nanostructure on a AgFON substrate varies from point to point, affecting the localized surface plasmon resonance, and accordingly, the SERS enhancement factor (Haynes et al., J. Phys. Chem. 107:7426 [2003]).

Temporal Stability of the EG3-Modified Substrate

Figure 17:
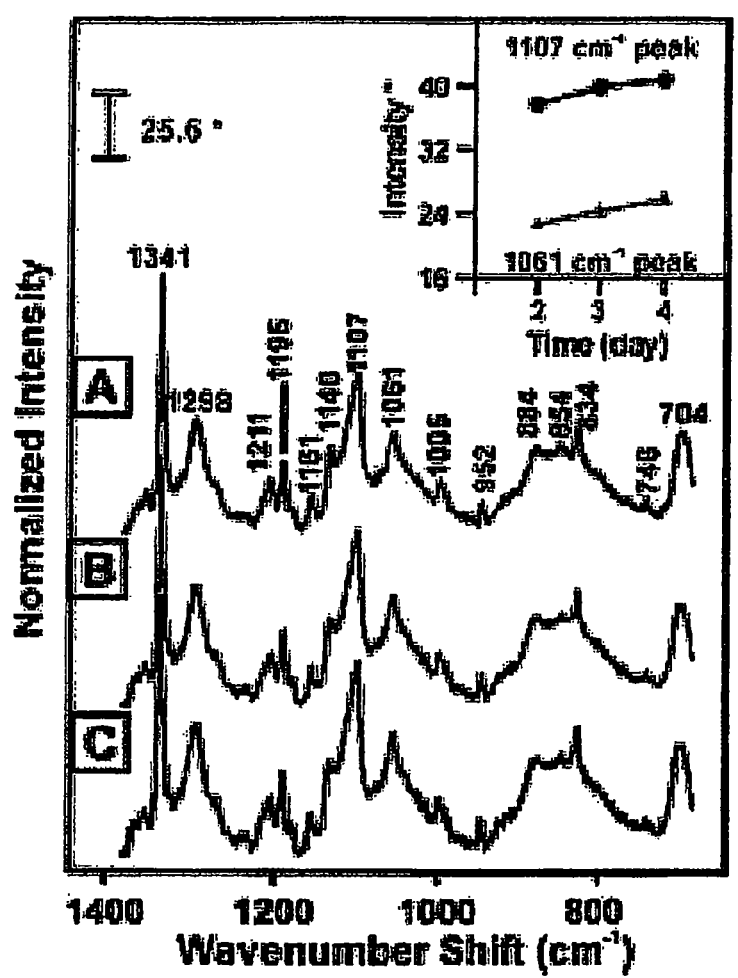
FIG. 17 shows SER spectra from nanobiosensors of the present invention captured every 24 hours from the same sample location for 72 hours.

It is preferred that implantable glucose sensors are stable for at least a three-day period (Kaufman et al., Diabetes Care 24:2030 [2001]). Previous work has demonstrated that bare AgFON surfaces display extremely stable SERS activity when challenged with high potentials (Dick et al., [2002]; supra) and high temperatures in ultrahigh Vacuum (Litorja et al., J. Phys. Chem. B 105:6907 [2001]). Here, the stability of the EG3-modified AgFON SERS substrate is studied over a period of three days in saline with pH=7.4 at room temperature. SER spectra were captured every 24 hours from the same sample location ($\lambda$ex=632.8, acquisition time (t)=60 s) (FIG. 17). The EG3 spectral band positions do not vary significantly over the course of 72 hours. Peaks at 1107 and 1064 cm-1 increase in intensity by 7.5% and 13% over 48 hours, respectively (inset in FIG. 17). The molecular order of self assembled monolayers (SAMs) increases with incubation time (Biebuyck et al., Langmuir 10:1825 [1994]); the rearrangement of the SAM gives rise to peaks with increasing intensity. The SERS peaks at 1341 and 834 cm-1 have been identified as a signature of highly ordered SAMs (Clarke et al., J. Phys. Chem. B 103: 8201 [1999]; Gregory et al., J. Phys. Chem. B 105:4684 [2001]) and are the subject of further investigation.

Reversible Glucose Sensing

Figure 18:
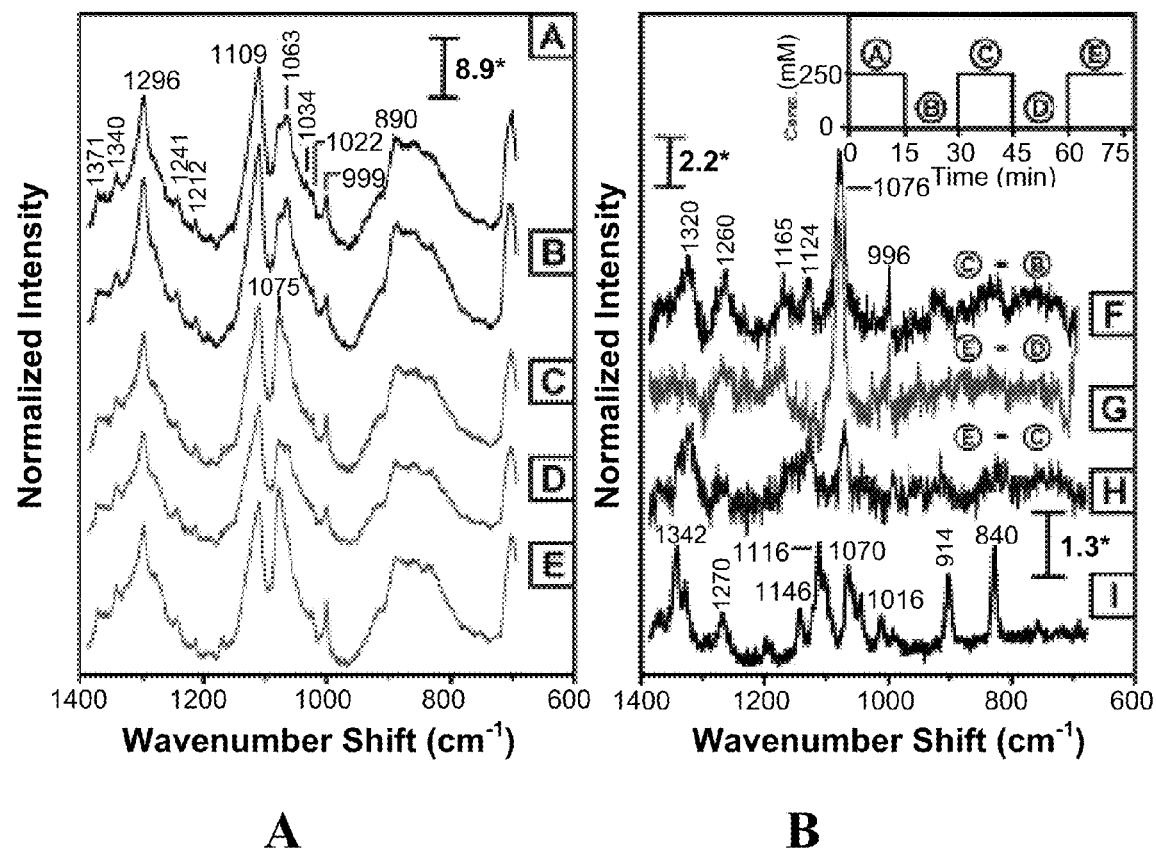
FIG. 18 shows SER spectra demonstrating the partition/departition capability of the EG3-modified AgFON substrate used in some embodiments of the present invention.

While the quantitative detection of glucose using the EG3-modified AgFON sensor and the stability of the sensor have been demonstrated, an implantable sensor is preferably reusable. In order to examine the partition/departition capability of the EG3-modified AgFON sensor, it was exposed to cycles of 250 mM and 0 mM glucose solutions (FIG. 18 inset). SER spectra were captured after each concentration variation ($\lambda$ex=632.8, Plaser=1.5 mW, t=30×20 s) (FIG. 18A). F and G are the difference spectra representing glucose partitioned into the EG3 SAM. I is the Raman spectrum of crystalline glucose for comparison. Vibrational modes at 1342 cm$^{-1}$ (C—C—H bend), 1270 cm-1, 1164 cm-1, 1116 cm$^{-1}$ (C—C+ C—O stretch), 1070 cm$^{-1}$ (C1-OH stretch), 914 cm-1 (O—C1-H1 bend), and 840 cm$^{-1}$ (C—C stretch) are known to be signatures of crystalline glucose (Soderholm et al., J. Raman Sprectrosc. 30:1009 [1999]). The literature has shown that SER spectral bands shift up to 25 cm-1 when compared to the normal Raman scattering bands of the same analyte (Stacy et al., Chem. Phys. Lett. 102:365 [1983]). Peaks in the SERS difference spectrum (FIG. 18; spectra F) at 1320, 1260, 1168, 1124, and 1076 cm-1 correspond with the Raman spectrum of crystalline glucose. In order to evaluate the glucose departitioning, spectral subtraction of two glucose-containing cycles was performed (FIG. 18; spectra H). Spectra H shows spectral features that match with the glucose peaks at 1320 and 1076 cm-1, but with lower intensities. Based on the 1076 cm-1 peak area, up to 33% of the glucose may remain in the EG3 layer after the 0 mM glucose cycle. The high glucose concentration used in this experiment caused incomplete departitioning after each cycle, and accordingly, the glucose accumulated in each step. However, it is contemplated that physiological concentrations (0-450 mg/dL, 0-25 mM) of glucose will not likely cause such accumulation in the partition layer, and the natural flow of aqueous humor (Vanlandingham et al., Am. J. Ophthal. 126:191 [1998]) and interstitial fluid will assist glucose departitioning.

Figure 19:
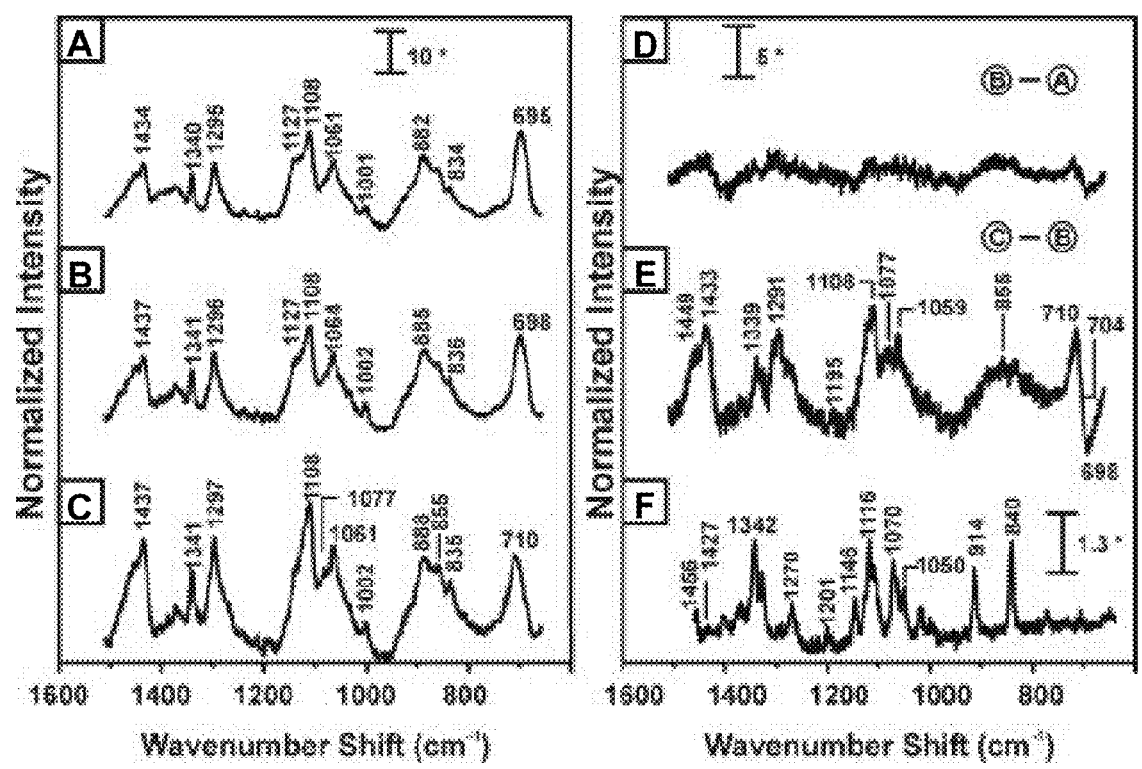
FIG. 19 shows SER spectra of the detection of glucose in presence of serum albumin.

Selectivity of the Sensor for Glucose in the Presence of Blood Serum Protein Mimic Quantitative detection, temporal stability, and reusability are preferred characteristics of a viable biosensor. It is also preferred that the glucose sensor be effective in the presence of interfering proteins. Serum albumin is a blood serum protein mimic for challenging the glucose sensor. In this work, 1 mg/mL serum albumin in saline was used after it was centrifuged, and the supernatant was filtered to remove any undissolved particulate. FIG. 18; spectra A shows the SER spectrum of the EG3-modified AgFON substrate in saline ($\lambda$ex=632.8, Plaser=0.8 mW, acquisition time (t)=240 s). When the serum albumin solution was injected into the flow cell, the SERS spectrum was collected throughout the 240-second incubation (FIG. 19; spectra B). Finally, the sample was exposed to 100 mM glucose, and the SER spectrum was collected (FIG. 19; spectra C). Spectra D is the difference spectrum demonstrating that serum albumin does not have a measurable SER spectrum. The present invention is not limited to a particular mechanism. Indeed, an understanding of the mechanism is not necessary to practice the present invention. Nonetheless, it is contemplated that the lack of SERS serum albumin bands is either due to the small Raman scattering cross section of serum albumin or inefficient adsorption of serum albumin to the EG3 partition layer. Spectra E demonstrates that the SERS glucose sensor is still effective after substrate exposure to an interfering protein. The peaks at 1449, 1433, 1339, 1291, 1108, 1077, 1059, and 855 cm$^{-1}$ (FIG. 19; spectra E) correspond with the crystalline glucose peaks shown in spectra F. This experiment shows that glucose partitioning into EG3 is not affected by the presence of large molecules such as serum albumin. The peak at 695 cm$^{-1}$ (FIG. 19; spectra A) shifts to 710 cm$^{-1}$ (spectra C) in the presence of glucose. This shift may be due to the rearrangement of the SAM when the glucose molecules partition into EG3. The observed shift further supports the hypothesis of glucose penetrating deeply into the EG3 monolayer, affecting even the character of the C—S bond.

Example 3

In Vivo Glucose Analysis

In some embodiments, an in vivo animal system is used to test the nanobiosensors of the present invention. A SERS biosensor (e.g., a fiber optic glucose sensor) is quantified in 10 Sprague-Dawley rats. Diabetes is induced with a single injection of streptozotocin (35 mg/kg) given IP. The blood glucose levels of each rat are measured daily using blood drawn from the dorsal tail vein until a diabetic state is confirmed by glucose measurements over 200 mg/dL.

In order to implant the sensors, the rats are anesthetized with 50 mg/kg sodium pentobarbital given IP. Every hour, or earlier if the rat responds to external stimuli, an additional dose (⅓ of the original dose) is given. The hair on the abdomen of the animal is removed with an electric razor following assurance that the animal does not feel pain. The skin is then scrubbed with a tamed iodine soap. Subsequent to sterilization of the skin surface, an approximately 10 mm long incision is made in the abdominal skin. A separation in the fascial plane between the skin and underlying abdominal muscles is created using blunt dissection with sterile surgical scissors and forceps. Prior to delivery, the optical fiber tip is placed ⅔ of the way down the barrel of a standard 25 gauge hypodermic needle. The barrel of the needle and fiber are passed through a silicon membrane such that when the membrane sits flush on the rat skin surface the fiber tip is just subcutaneous. The membrane adheres to the surface of the rat skin. The needle is then withdrawn from the skin leaving the optical fiber tip in place. The membrane closes around the optical fiber, holding it firmly. The fiber is held in place with a suture or adhesive and the skin is closed with 5-0 nylon suture.

The proximal end of the optical fiber is connected to instrumentation for collection of Raman spectra. The glucose levels of the rats are varied by IV injection of glucose and insulin thru an indwelling IV catheter. The actual blood glucose is monitored using a standard laboratory system (e.g., those commercially available from YSI or Beckman). The glucose level is varied from approximately 40-500 mg/dL. The glucose concentration in interstitial fluid is allowed to stabilize for approximately 10-15 minutes and then Raman spectra are collected continuously. The sensor is left in place for at least 5 days to monitor the accuracy and durability of the sensor. The rats are euthanized with an overdose of sodium pentobarbital (150 mg/kg) given IP following surgery.

The collected Raman spectra are analyzed chemometrically and interstitial glucose levels are determined and correlated with blood glucose measurements. The results are plotted on a Clarke error grid.

The rat model is also used to test the control of glucose levels using a feedback loop and insulin delivery system. The diabetic rat is constrained and catherized for infusion of glucose and insulin and withdrawal of blood for glucose measurements. Insulin is delivered subcutaneously using a standard catheter set from MiniMed via a catheter connected to a motor-driven syringe pump. The speed of insulin delivery (i.e., the motor speed) is modulated based on the glucose level. A proportional-integral-differential (PID) controller with upper and lower limit constraints in the feedback loop is used to determine the amount of insulin to be injected. Initial active variation in the PID parameters is used to achieve reasonable control with limited oscillations in the blood glucose. The control system is challenged with periodic injections of glucose and insulin.

Example 4

Biosensors Utilizing Decanethiol/Mercaptohexanol Partition Layers

This Example describes characterization of glucose-sensing biosensors comprising decanethiol/mercaptohexanol mixed partition layers as an example of multiple component SAMs.

A. Methods

Materials

All the chemicals were reagent grade or better, and used as purchased. Silver pellets (99.99%) were purchased from Kurt J. Lesker Company (Clairton, Pa.). Oxygen free high conductivity copper was obtained from McMaster-Carr (Chicago, Ill.) and cut into 18 mm diameter disks. To clean substrates, $NH_4OH$, $H_2O_2$, and $CH_3CH_2OH$ were used from Fisher Scientific (Fairlawn, Va.). Surfactant-free, white carboxyl-substituted latex polystyrene nanosphere suspensions (390+19.5 nm diameter, 4% solid) were purchased from Duke Scientific Corporation (Palo Alto, Calif.). Ultrapure water (18.2 MΩcm$^{-1}$) from a Millipore system (Marlborough, Mass.) was used for substrate and solution preparation. Bovine plasma was obtained from Hemostat Laboratories (Dixon, Calif.). Glucose, lactate, and urea were purchased from Sigma (St. Louis, Mo.). Decanethiol ($CH_3(CH_2)_9SH$), and 6-mercapto-1-hexanol ($HS(CH_2)_6OH$) were purchased from Aldrich (Milwaukee, Wis.). Disposable filters, pore size 0.45 µm, were acquired from Gelman Sciences (Ann Arbor, Mich.).

AgFON Fabrication and Incubation Procedure

Figure 20:
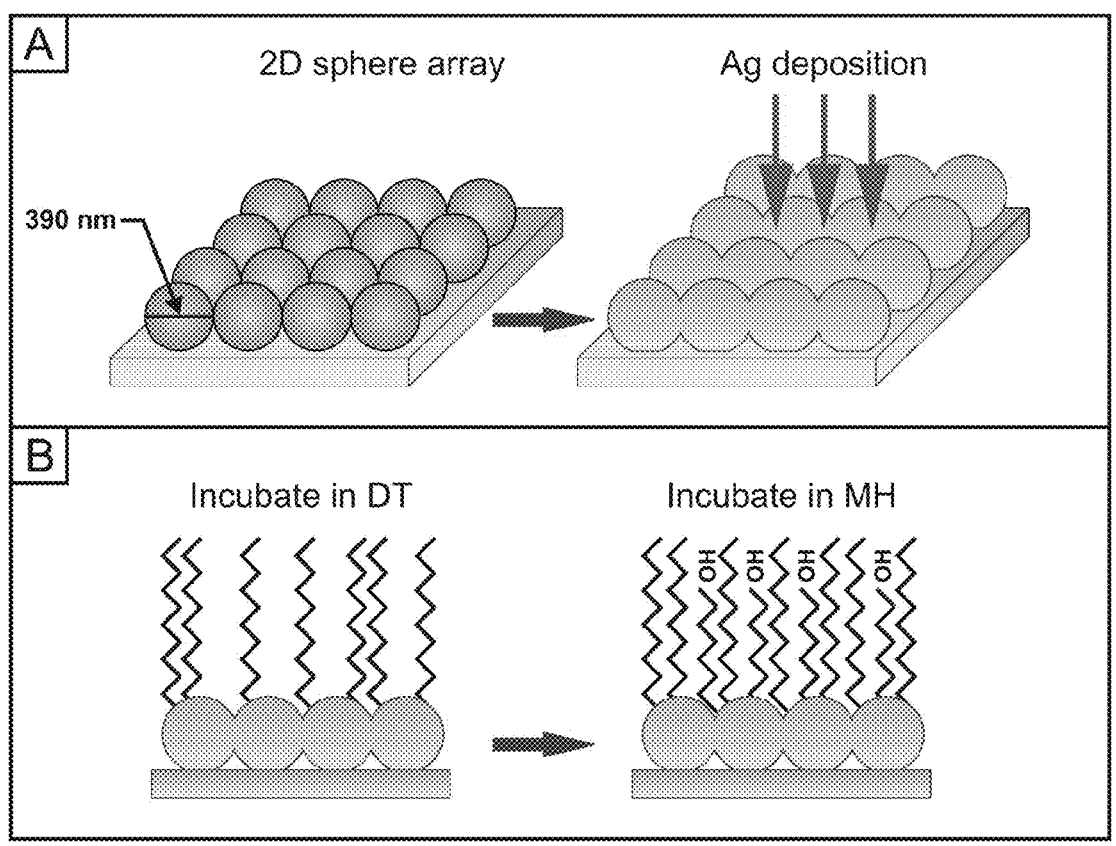
FIG. 20 shows a schematic diagram for fabricating DT/MH-functionalized AgFON.

The copper substrates were cleaned by sonicating in 5:1:1 $H_2O/30\% H_2O_2/NH_4OH$. Approximately 10 µl of nanosphere solution was drop-coated onto a clean copper substrate and allowed to dry at room temperature. Then, 200 nm thick Ag films were deposited onto and through the nanosphere mask using the Kurt J. Lesker electron beam deposition system (Clairton, Pa.) to form AgFON substrates. The mass thickness and deposition rate (2 Å/s) of the Ag metal were measured by 6 MHz gold plated quartz-crystal microbalance purchased from Sigma Instruments (Fort Collins, Colo.). AgFON substrates were first incubated in 1 mM DT in ethanol for 45 minutes and then transferred to 1 mM MH in ethanol for at least 12 hours (FIG. 20). Then the SAM-functionalized surfaces were mounted into a small volume flow cell for SER spectra collection.

Surface-enhanced Raman Spectroscopy

A Spectra-Physics model Millennia Vs laser ($\lambda_{ex}$=532 nm) was used to excite a Spectra-Physics model 3900 Ti-sapphire laser to produce the 785 nm excitation wavelength ($\lambda_{ex}$); the laser spot size on the sample was less than 0.5 mm in diameter. This excitation wavelength was chosen to minimize autofluorescence of proteins (Anderson and Parrish, *The Sci-* ence of Photomedicine; Plenum Press: New York, p 147 [1982]; Weissleder, Nat. Biotechnol. 19:316 [2001]). The SERS measurement system includes an interference filter, an edge filter (Semrock, Rochester, N.Y.), a model VM-505 single-grating monochromator with the entrance slit set at 100 μm (Acton Research Corp., Acton, Mass.), and a $LN_2$-cooled CCD detector (Roper Scientific, Trenton, N.J.). A collection lens with magnification 5 was used to collect the scattered light. The small volume flow cell was used to control the external environment of the AgFON surfaces throughout the SERS experiments.

Quantitative Multivariate Analysis

All data processing was performed using MATLAB (MathWorks, INC., Natick, Mass.) and PLS_Toolbox (Eigenvector Research, Inc., Manson, Wash.). Prior to analysis, the spectra were smoothed using the Savitsky-Golay method with a second order polynomial and window size of 9. Cosmic rays were removed from the spectra using a derivative filter. The slowly varying background, commonly seen in SERS experiments was removed by subtracting a fourth-order polynomial fit. This method greatly reduced varying background levels with minimum effect on the SERS peaks. The chemometric analysis was performed using the partial least-squares (PLS) method and leave-one-out (LOO) cross validation algorithm.

Time Constant Analysis

The data was processed using PeakFit 4.12 software (Systat Software Inc, Richmond, Calif.). To remove the varying background in SER spectra, a fourth order polynomial was subtracted from the baseline using MATLAB software. The spectra were further preprocessed in PeakFit with linear best fit baseline correction and Savitsky-Golay smoothing. The amplitude of the Raman bands was obtained by fitting the data to the superposition of the Lorentzian amplitude lineshapes.

B. Results

The results presented below show significant advancement towards an implantable, real-time continuous SERS based glucose sensor. Our previous work (See Example 1) demonstrated the ability to detect glucose with SERS using decanethiol as the partition layer. Subsequently, EG3 was used as the partition layer because it is biocompatible and has the ability to resist nonspecific binding of proteins. (See Example 2). Moreover, stability, reversibility, and resistance to serum protein interference of the EG3-functionalized glucose sensor were demonstrated. Finally, the SERS based glucose sensor was optimized for NIR laser excitation wavelength with the EG3 partition layer to reduce photodamage of tissue and optimize signal on Au surfaces (Stuart et al., Anal. Chem. 77: 4013 [2005]). This development showed enhanced spectral stability and gave more accurate measurements. However, due to the intricate synthesis, availability of EG3 is scarce. In the present Example, a new mixed SAM layer, consisting of decanethiol (DT) and mercaptohexanol (MH) has been developed. We also demonstrate (1) long term stability of the DT/MH-functionalized AgFON surface (2) reversibility of the sensor (3) quantitative measurement of glucose, and (4) real-time partitioning and departitioning of the glucose sensor.

Temporal Stability of DT/MH-Modified Substrate.

Figure 21:
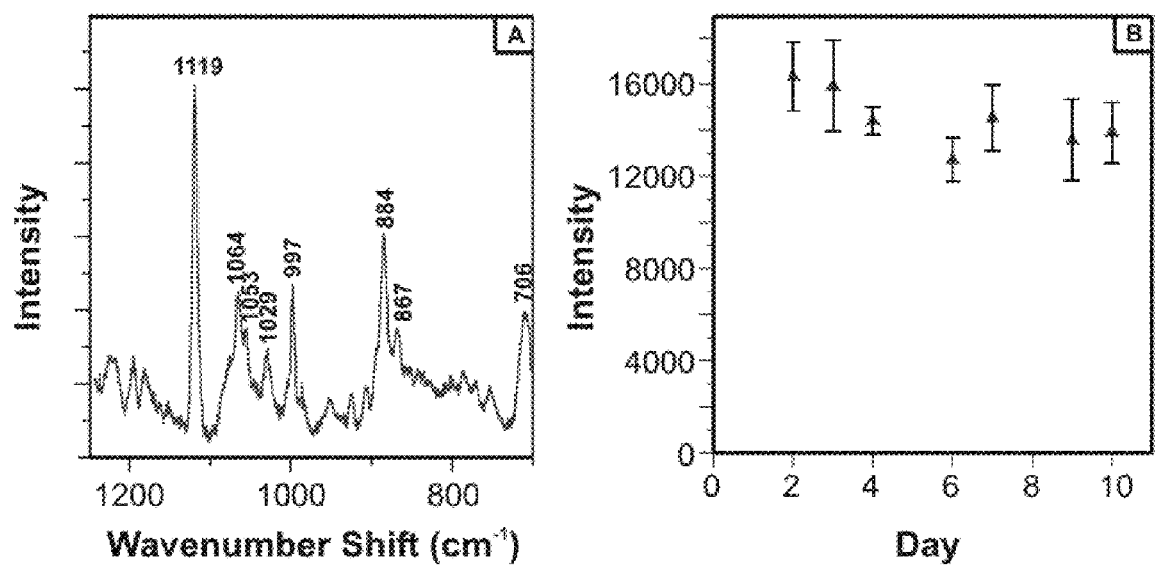
FIG. 21 shows the temporal stability of the DT/MH-functionalized FON.

An implantable glucose sensor must be stable for at least 3 days (Heller, Annu Rev. Biomed. Eng. 1:153 [1999]). In previous work, we have demonstrated that SAM-functionalized AgFON substrates were stable for at least 3 days in phosphate buffered saline by electrochemical and SERS measurements (Stuart et al., Anal. Chem. 77:4013 [2005]). Here, we demonstrate the stability of the DT/MH-functionalized AgFON surface for 10 days in bovine plasma (FIG. 21). SER spectra were captured every 24 hours from three different samples and three spots on each sample ($\lambda_{ex}$=785 nm, acquisition time (t)=2 min). FIG. 21A represents the DT/MH spectrum acquired on day 2. FIG. 21B shows the average intensity of the 1119 $cm^{-1}$ peak for DT/MH on the AgFON for each day as a function of time. The 1119 $cm^{-1}$ band corresponds to a symmetric stretching vibration of a C—C bond (Bryant et al., J. Am. Chem. Soc. 113, 8284, [1991]). The change in intensity of the 1119 $cm^{-1}$ peak from the first day to the last day is 2.08%, indicating that it did not vary significantly during the ten day period. The 2% change in the intensity can be attributed to the rearrangement of the SAM during the incubation in bovine plasma (Biebuyck et al., Langmuir 10:1825 [1994]). The temporal stability of the 1119 $cm^{-1}$ peak intensity indicates that the DT/MH SAM was intact and well ordered, making this SAM-functionalized surface a potential candidate for an implantable sensor.

Reversible Glucose Sensing

Figure 22:
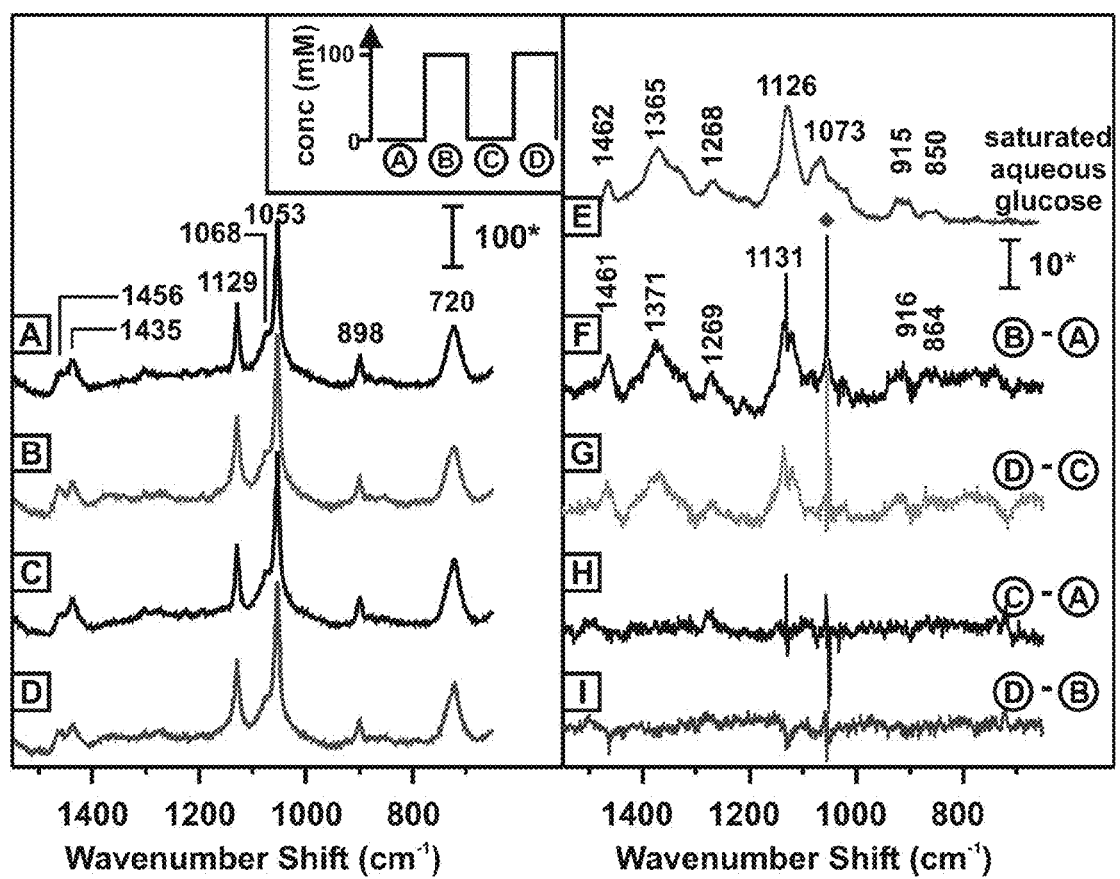
FIG. 22 shows a glucose pulsing sequence on the SAM modified AgFON surface (inset). SERS spectra of the sample cycled between 0 and 100 mM aqueous glucose solutions (spectra A, B, C, D), $\lambda_{ex}$=532 nm, $P_{laser}$=10 mW, acquisition time (t)=20 min, pH~7. Spectrum E shows the normal Raman spectrum of aqueous saturated glucose solution. Difference spectra F, G, H, and I show the partitioning/departitioning of glucose. Note that imperfect subtraction of the narrow band at 1053 cm$^{-1}$ due to nitrate results in a very sharp peak in the difference spectra (diamond).

An implantable glucose sensor must also be reversible in order to successfully monitor fluctuation in glucose concentration throughout the day. To demonstrate the reversibility of the sensor, the DT/MH-modified AgFON sensor was exposed to cycles of 0 and 100 mM aqueous glucose solutions (pH~7) without flushing the sensor in between measurements to simulate real-time sensing (FIG. 22 inset). Nitrate was used as an internal standard in all the experiments (1053 $cm^{-1}$ peak) to minimize effective laser power fluctuations. The 1053 $cm^{-1}$ band corresponds to a symmetric stretching vibration of $NO_3^-$ and was used to normalize the spectra (Soderholm et al., J. Raman Spectrosc. 30:1009 [1999]). SERS spectra were collected for each step ($\lambda_{ex}$=532 nm, P=10 mW, acquisition time (t)=20 min) (FIG. 22A, 22B, 22C, 22D). FIG. 22E shows the normal Raman spectrum of a saturated aqueous glucose solution for comparison. In the normal Raman spectrum of a saturated aqueous glucose solution, peaks at 1462, 1365, 1268, 1126, 915, and 850 $cm^{-1}$ correspond to crystalline glucose peaks. The difference spectra (FIG. 22F, 22G) represent partitioning of glucose in DT/MH SAM, which clearly show the glucose features at 1461, 1371, 1269, 1131, 916, and 864 $cm^{-1}$. This corresponds to the peaks in the normal Raman spectrum of glucose in aqueous solution (FIG. 22E). SERS bands can shift up to 25 $cm^{-1}$ when compared to normal Raman bands of the same analyte (Stacy et al., Chem. Phys. Lett. 102:365 [1983]). The sharp peak seen in all of the difference spectra at 1053 $cm^{-1}$ represent imperfect subtraction of the nitrate internal standard. The absence of glucose spectral features in the difference spectra (FIG. 22H, 22I) represents complete departitioning of glucose. The DT/MH mixed SAM presents a completely reversible sensing surface for optimal partitioning and departitioning of glucose.

Quantitative Detection of Glucose Using DT/MH Partition Layer

Figure 23:
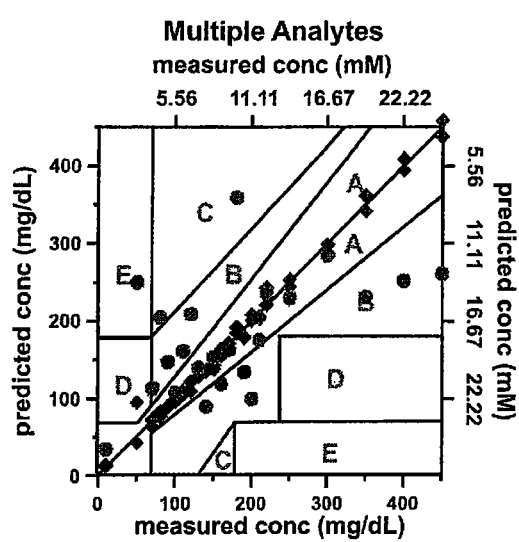
FIG. 23 shows calibration (♦) and validation (●) plots using two substrates and multiple spots. A PLS calibration plot was constructed using 46 data points. The validation plot was constructed using 23 data points taken over a range of glucose concentrations (10-450 mg/dL) in 1 mM lactate and 2.5 mM urea at pH~7. RMSEC=9.89 mg/dL (0.55 mM) and RMSEP=92.17 mg/dL (5.12 mM). $\lambda_{ex}$=785 nm, $P_{laser}$=8.4 mW, acquisition time (t)=2 min.

In order for a glucose sensor to be viable, it should be able to detect glucose in the clinically relevant range 10-450 mg/dL (0.56-25 mM), under physiological pH, and in the presence of interfering analytes (FIG. 23). The data is presented in the Clarke error grid, a standard for evaluating the reliability of glucose sensors in the clinically relevant concentration range (0-450 mg/dL) (Clarke et al., Diabetes Care 10:622 [1987]). Data points that fall in the A and B range are acceptable values. Values outside the A and B range result in potential failure to detect blood glucose levels outside of the target range and erroneous diagnosis. DT/MH-functionalized AgFON samples were placed in a flow cell containing water (pH~7) with lactate (1 mM) and urea (2.5 mM) in physiological concentrations, which are potential interferents for glucose detection. Glucose solutions ranging from 10 to 450 mg/dL with lactate and urea were then randomly introduced in the cell and incubated for 2 min to ensure complete partitioning. SER spectra were collected using two substrates and multiple spots with a near-infrared laser source ($\lambda$=785 nm, P=8.4 mW, acquisition time (t)=2 min). A calibration model was constructed using partial least squares leave-one-out (PLS-LOO) analysis with 46 randomly chosen independent spectral measurements of known glucose concentrations. The calibration model was based upon 7 latent variables that take into account variation in laser power, the environment in the lab, and SERS enhancement at different locations. The PLS analysis results in a root mean square error of calibration (RMSEC) of 9.89 mg/dL (0.549 mM). This RMSEC value is lower than that reported in our previous work using the EG3-modified AgFON.

In addition to having a low RMSEC, it is important to use an independent validation set to test the calibration model (Beebe et al., Chemometrics: A Practical Guide; Wiley Interscience: New York, [1998]). For this model, a set of 23 data points was used to validate the model. The root mean square error of prediction (RMSEP) was calculated to be 92.17 mg/dL (5.12 mM). FIG. 23 depicts that 98% of the calibration points and 87% of the validation points fall in the A and B range of the Clarke error grid. The RMSEP can be improved by increasing the number of data points in the calibration set.

Figure 24:
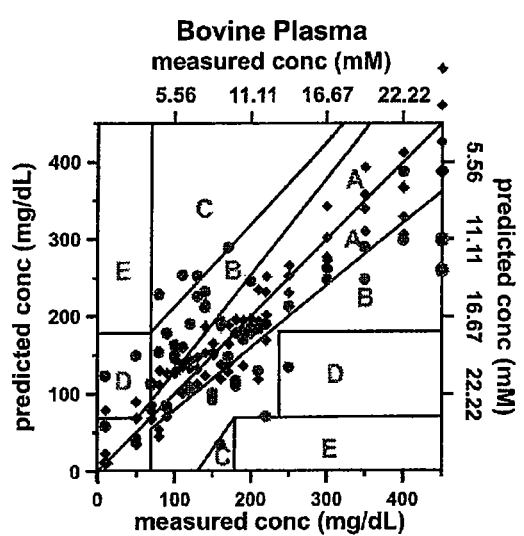
FIG. 24 shows calibration (♦) and validation (●) plots using three substrates and multiple spots acquired in two days. A PLS calibration plot was constructed using 92 data points. The validation plot was constructed using 46 data points taken over a range of glucose concentrations (10-450 mg/dL) in bovine plasma. RMSEC=34.3 mg/dL (1.9 mM) and RMSEP=83.16 mg/dL (4.62 mM). $\lambda_{ex}$=785 nm, $P_{laser}$=10-30 mW, acquisition time (t)=2 min.

To transition from the in vitro sensor to an in vivo sensor, the sensor should also demonstrate quantitative detection in a more complex medium. Bovine plasma was used to simulate the in vivo environment of an implantable glucose sensor. Prior to use, bovine plasma was filtered using 0.45 µm diameter pore size. The filtered plasma was then spiked with glucose concentrations ranging from 10-450 mg/dL. DT/MH-functionalized AgFON substrates were placed in the flow cell and exposed to glucose spiked bovine plasma. SERS spectra were collected at each concentration using multiple samples and multiple spots in random order to construct a robust calibration model ($\lambda_{ex}$=785 nm, P=10-30 mW, acquisition time (t)=2 min). Calibration was constructed using PLS-LOO analysis described above using 7 latent variables and presented in a Clarke error grid (FIG. 24). To construct the calibration, 92 randomly chosen data points were used, resulting in an RMSEC of 34.3 mg/dL (1.90 mM). For the validation, 46 data points were used with an RMSEP of 83.16 mg/dL (4.62 mM). In the Clarke error grid, 98% for calibration and 85% for validation fall in the A and B range. Errors in both experiments can be reduced by the use of additional data points for the calibration. In addition, error can also be attributed to variation in SERS enhancement at different spots and different substrates (Haynes et al., J. Phys. Chem. 107: 7426 [2003]). The results show that the DT/MH-modified AgFON glucose sensor is capable of making accurate glucose measurements in the presence of many interfering analytes.

Real-Time Study of Partitioning and Departitioning of Glucose

In addition to reversibility, which is an important characteristic for a viable sensor, the sensor should be able to partition and departition glucose on a reasonable time scale. The real-time response was examined in a system with bovine plasma simulating the in vivo environment. In order to evaluate the real-time response of the sensor, the 1/e time constant for partitioning and departitioning was calculated.

Figure 25:
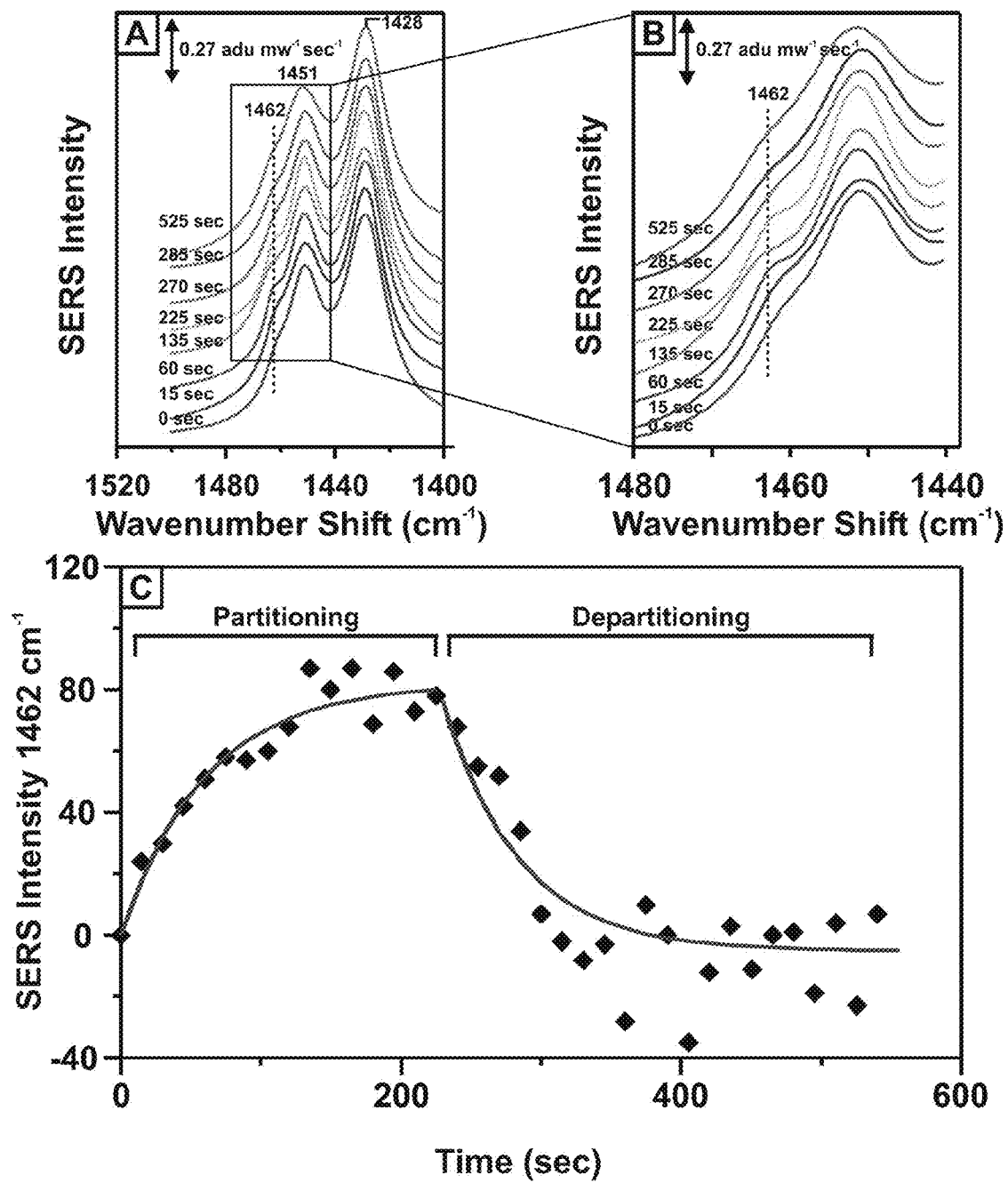
FIG. 25 shows real-time SERS responses to step changes in glucose concentrations in bovine plasma.

A DT/MH-functionalized AgFON was placed in bovine plasma for ~5 hours. The AgFON surface was then placed in a flow cell. SER spectra were collected continuously ($\lambda_{ex}$=785 nm) with a 15 second integration time. To observe partitioning, 50 mM glucose solution in bovine plasma was injected at t=0. At t=225 sec, 0 mM glucose solution in bovine plasma was injected into the flow cell to evaluate the departitioning of glucose. An excitation wavelength of 785 nm was used to reduce autofluorescence caused by proteins (Anderson and Parrish, The Science of Photomedicine; Plenum Press: New York, p 147 [1982], Weissleder, Nat. Biotechnol. 19:316 [2001]). The amplitude was then plotted versus time as shown in FIG. 25C. The 1/e time constant was calculated from the exponential curve fitted to the data points.

The spectra shown in FIGS. 25A and 25B demonstrate real-time amplitude changes in the 1462 cm$^{-1}$ peak as glucose concentrations vary. The amplitude of the 1462 cm$^{-1}$ peak was obtained by fitting the data to the superposition of three Lorentzian lineshapes using PeakFit. The 1/e time constant is 28 seconds for partitioning, and 25 seconds for departitioning, calculated from the exponential fit (FIG. 25C). These experiments demonstrate that partitioning and departitioning occur rapidly making the DT/MH SERS-based glucose sensor suitable for implantable, continuous sensing.

Example 5

In Vivo Glucose Analysis

This Example describes the characterization of glucose-sensing biosensors comprising DT/MH partition layers in vivo.

A. Methods

Materials

Figure 26:
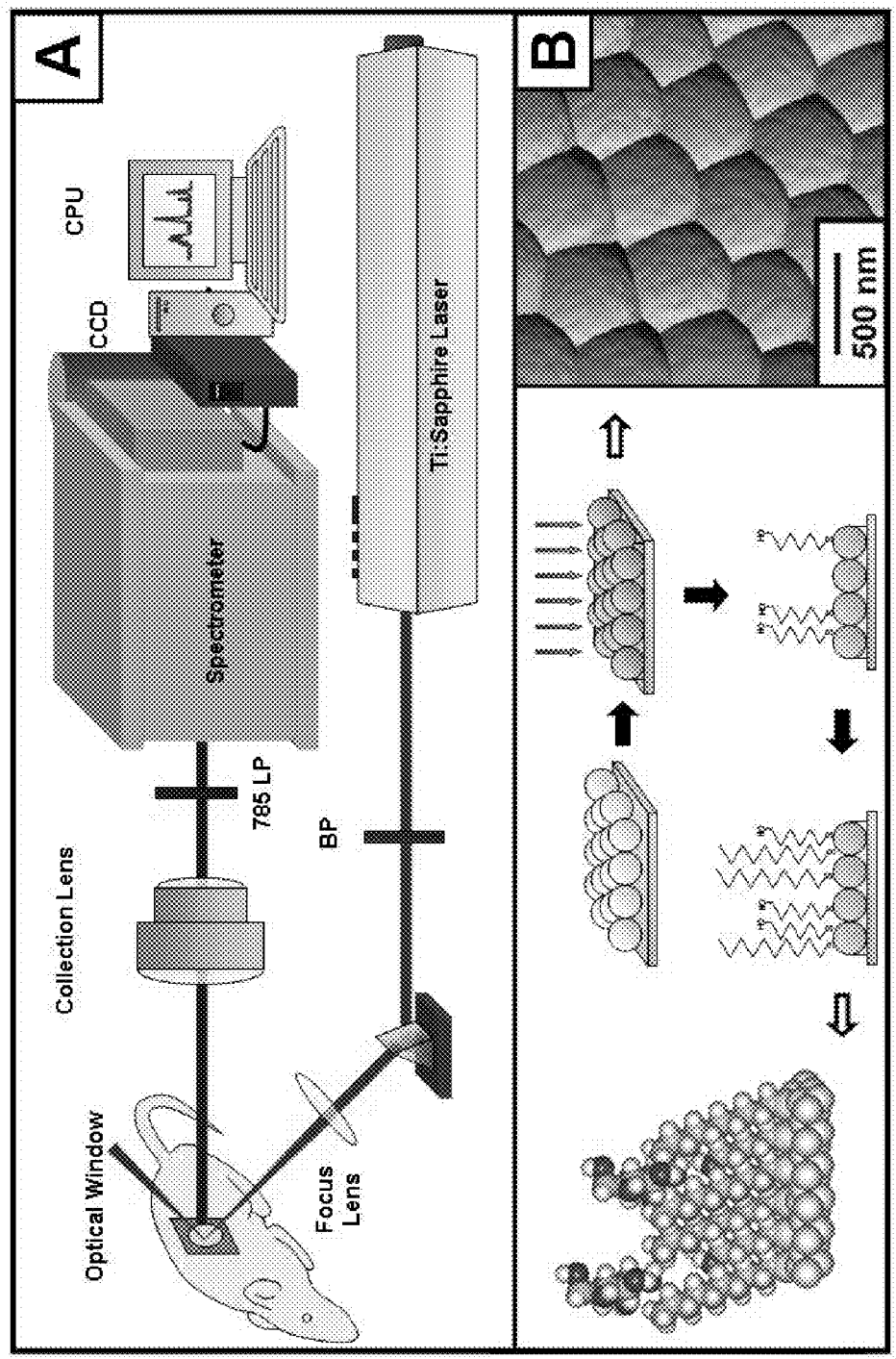
FIG. 26 shows a schematic diagram of the instrumental apparatus (FIG. 26A) and substrate preparation (FIG. 26B) used for in vivo experiments.

The SAM functionalized SERS active surfaces were prepared in two steps, as shown in FIG. 26. First, AgFON surfaces were fabricated by drop-coating 10 µl of 390 nm diameter nanosphere solution onto clean copper substrates, and then depositing a 200-nm-thick Ag film onto the nanosphere mask. The AgFON substrates were then incubated in 1 mM decanethiol (DT) for 45 minutes and subsequently transferred to 1 mM mercaptohexanol (MH) solution for at least 12 hours to form a mixed DT/MH SAM. The substrates were kept in 1 mM MH in ethanol prior to surgically implantation.

Animal Care and Preparation

The surgical procedure followed the protocol filed with Northwestern University and in accord with IACUC provisions. Sprague-Dawley rats (300-500 g, N=4 were anesthetized with pentobarbital (Office of Research Safety, Northwestern University) with an initial dose of 50 mg/kg IP. The animals were checked for pain reactions by toe-tug and blink tests. The rats were kept anesthetized by hourly administration of pentobarbital at 25 mg/kg. After the anesthetic had taken effect, the surgical areas were prepared by removal of hair (shaving and chemical depilatory) and cleaning. Then, the femoral vein was cannulated using PE 50 tubing (Clay Adams) for glucose injections. The carotid artery was cannulated with PE 90 tubing for blood glucose measurements with FDA-qualified home medical equipment (One Touch II Meter). A tracheotomy and intubation was performed to enable the attachment of a ventilator to aid breathing. The incisions were shut with surgical clips. The rat was thermally stabilized by an electric heating pad throughout the course of the surgery and experiment. A metal frame containing a glass window was placed along the midline of the rat's back. A circular incision was made to allow the positioning of a DT/MH functionalized AgFON substrate subcutaneously such that the substrate was in contact with the interstitial fluid, and optically addressed through the window. Following the experiment, the animals were sacrificed with an overdose of anesthetic and bilateral thoracotomy.

Experimental Protocols

Glucose was varied in the rat through intermittent intravenous infusion for three hours. A bolus of glucose was delivered over 5 to 10 min, at a concentration of 1 g/mL in sterile phosphate buffered saline. A droplet of blood was drawn from the rat, the glucose level was measured with the One Touch II glucometer, and corresponding SERS measurements were taken. The SERS spectra were acquired through the optical window using a Ti:Saph laser ($\lambda_{ex}$=785 nm, P=50 mW, acquisition time (t)=2 min).

Data Analysis

Figure 27:
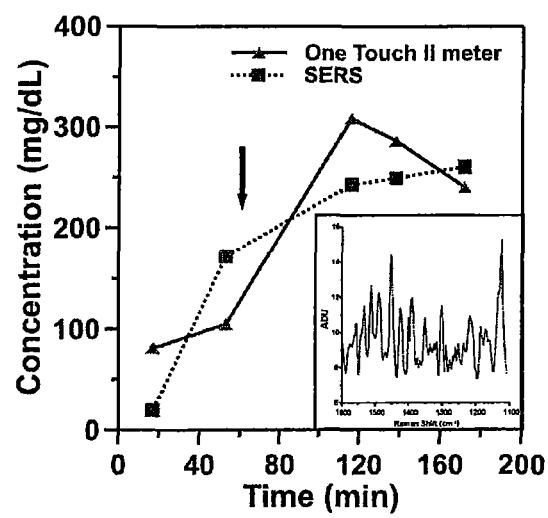
FIG. 27 shows the time course of an in vivo glucose measurement experiment. Paired data from FIG. 27 are displayed versus time of acquisition, plotting the glucose concentration change over time. The glucose bolus was started at t=60 min. Triangles (▲) represent measurements made using a One Touch II blood glucose meter, and squares (■) represent measurements made using a SERS sensor. The glucose infusion was started at 1 hour, as demarcated by the arrow. The inset shows an exemplary in vivo SERS spectrum after baseline correction and smoothing. ($\lambda_{ex}$=785 nm, P=50 mW, t=2 min).
Figure 28:
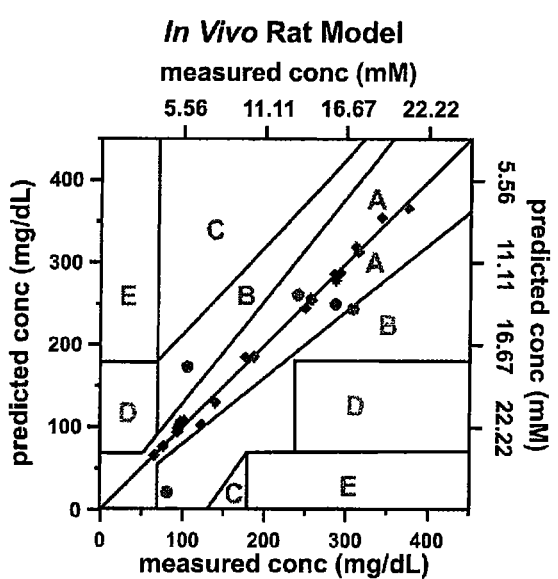
FIG. 28 depicts an exemplary Clarke glucose error grid analysis showing in vivo data from calibration (♦) and validation (●) plots using a single substrate and a single spot on a DT-MH functionalized AgFON surface. The calibration set was constructed using 21 data points correlated with a commercial glucometer. The validation set was constructed using 5 data points. RMSEC=7.46 mg/dL (0.41 mM) and RMSEP=53.42 mg/dL (2.97 mM). ($\lambda_{ex}$=785 nm, P=50 mW, acquisition time (t)=2 min).

The data were collected and analyzed by the partial least squares method (Yonzon et al., Analytical Chemistry 76:78 [2004]; Stuart et al., Analytical Chemistry 77:4019 [2005]; Lyandres et al., Analytical Chemistry 77:6134 [2005]; Shafer-Peltier et al., Journal of the American Chemical Society 125:588 [2003]). FIG. 27 shows corresponding glucose concentration variations in an exemplary rat using SERS and the One Touch II blood glucose meter. Both the standard glucometer and the SERS-based measurements tracked the change in glucose concentration after infusion i.e., a sharp rise in glucose concentration is detected by both techniques after the start of the glucose infusion (t=60 min). FIG. 28 plots the time-independent data on the Clarke error grid to more precisely gauge the performance of the SERS measurement system. The Clarke error grid was developed as a convenient and modality-independent means to compare the accuracy and performance of glucose sensors in the clinically relevant range Clarke et al., Diabetes Care 10:622 [10987]). The grid is divided into five zones. Predictions within these zones lead to: A) clinically correct measurement and treatment, B) benign errors or no treatment, C) incorrect measurements leading to overcorrection of acceptable glucose levels, D) dangerous failure to detect and treat, and E) treatments that further aggravate abnormal glucose levels.

B. Results

The majority of measurements from all samples fell within the acceptable range. FIG. 28 shows a representative Clarke error grid analysis of a single rodent. The 26 measurements are from a single spot on the implanted DT/MH functionalized AgFON surface. The calibration set was constructed using 21 data points that were correlated with the commercial glucometer. The validation set was constructed using 5 independent data points. The sensor had relatively low error (RMSEC=7.46 mg/dL (0.41 mM) and RMSEP=53.42 mg/dL (2.97 mM). These data compare favorably with our previous in vitro results (See Examples 1, 2 and 4) as well as those of other optically based glucose measurements Solnica et al., J. Clinica Chimica Acta 331:29 [2003]).

Figure 29:
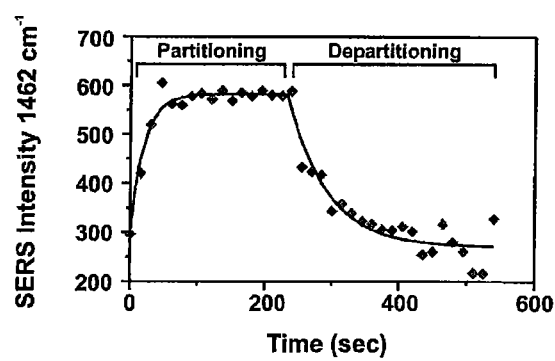
FIG. 29 shows an ex vivo analysis of nanobiosensor response time. Real-time SERS were recorded in response to step changes in glucose concentration after being implanted in a rat for 5 hours and then removed. Glucose was injected into the flow cell at t=0 sec, and the cell was then flushed with bovine plasma at t=225 sec.

Important parameters governing the overall efficacy of a given sensor are its response time, reversibility, and long-term stability. Previous research has demonstrated that FON based sensors are stable with good reversibility under a variety of conditions. The present work shows that the SERS sensors of the present invention show rapid response to detect the glucose injection, keeping pace with a conventional glucometer. Because it is impossible to rapidly and accurately vary glucose levels in vivo, additional in vitro experiments were conducted to determine whether the sensor is capable of exhibiting response times rapid enough for continuous or semi-continuous monitoring (i.e., ≤the 2 min collection time). After being implanted in the rat for 5 hr, a DT/MH functionalized AgFON surface was removed and placed in a flow cell containing bovine plasma to simulate the in vivo environment. Then, the 1/e time constant response to a step change in glucose concentration was determined (FIG. 29). The AgFON surface was exposed to 50 mM glucose in plasma at t=0 seconds and then flushed with plasma at t=225 seconds. SERS spectra were collected every 15 seconds ($\lambda_{ex}$=785 nm, P=100 W). Based upon amplitude calculations for the 1462 $cm^{-1}$ peak, the 1/e time constant was 9 seconds for partitioning, and 27 seconds for departitioning. These values indicate that glucose binds reversibly to the SERS active surface, and that changes in concentration as rapid as ~30 seconds can be detected spectroscopically.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the present invention.

We claim:

1. A method for the in vivo determination of glucose concentration, comprising:
   a) contacting an implanted biosensor with a bodily fluid to create a biosensor-glucose ensemble:
      i) wherein said bodily fluid comprises glucose,
      ii) wherein said implanted biosensor comprises,
         1. a substrate,
         2. nanospheres, said nanospheres in contact with said substrate,
         3. a metal film, said metal film formed over said nanospheres, and
         4. a self-assembled mixed partition layer, said self-assembled mixed partition layer adhered to said metal film, said self-assembled mixed partition layer comprising at least two discrete compounds,
            a. said two discrete compounds comprising decanethiol and mercaptohexanol, and
      iii) wherein said glucose concentrates within the self-assembled mixed partition layer in close physical proximity to the metal film;
   b) directly detecting said glucose in said biosensor-glucose ensemble with surface-enhanced Raman spectroscopy to create a surface-enhanced Raman signal; and
   c) correlating said surface-enhanced Raman signal to the concentration of said glucose in said bodily fluid.

2. The method of claim 1, wherein said nanospheres comprise polystyrene or silica nanospheres.

3. The method of claim 1, wherein said implanted biosensor further comprises a receptor, said receptor attached to said self-assembled mixed partition layer, said receptor specific for said glucose, and wherein said receptor is configured to bind reversibly to glucose.

4. The method of claim 1, wherein said substrate is copper or silicon dioxide.

5. The method of claim 1 wherein said bodily fluid is blood.

6. The method of claim 1 wherein said bodily fluid is plasma.

7. The method of claim 1 wherein said bodily fluid is serum.

8. The method of claim 1 wherein said bodily fluid is interstitial fluid.

9. The method of claim 1 wherein said bodily fluid is extracellular fluid.

10. The method of claim 1 wherein close physical proximity comprises 1-2 nm.

* * * * *

UNITED STATES PATENT AND TRADEMARK OFFICE
CERTIFICATE OF CORRECTION

Page 1 of 1

PATENT NO. : 8,592,226 B2
APPLICATION NO. : 12/556436
DATED : November 26, 2013
INVENTOR(S) : Richard P. Van Duyne et al.

It is certified that error appears in the above-identified patent and that said Letters Patent is hereby corrected as shown below:

Title Page, Item (75) Inventor should read:

-- Matthew R. Glucksberg, Evanston, IL (US); --

In the Specification:

In Column 1, lines 19-26, the federal funding reads as follows:

-- This invention was made with government support under grant numbers EY013002, EY013015, and DK066990 awarded by the National Institutes of Health; grant numbers CHE0414554, EEC0118025 and DMR0076097 awarded by the National Science Foundation; grant number F49620-02-1-0381 awarded by the Air Force Office of Scientific Research; and grant number W8XWH-04-1-0630 awarded by the U.S. Army Medical Research and Materiel Command. The government has certain rights in the invention. --

Signed and Sealed this
Twenty-fifth Day of February, 2014

Michelle K. Lee
*Deputy Director of the United States Patent and Trademark Office*